United States Patent [19]

Alexander et al.

[11] Patent Number: 4,820,773

[45] Date of Patent: Apr. 11, 1989

[54] WATER ABSORBENT RESINS PREPARED BY POLYMERIZATION IN THE PRESENCE OF STYRENE-MALEIC ANHYDRIDE COPOLYMERS

[75] Inventors: William Alexander, Naperville; Mark Anderson, Wheaton; Barbara R. Regan, Glenview, all of Ill.

[73] Assignee: American Colloid Company, Arlington Heights, Ill.

[21] Appl. No.: 67,233

[22] Filed: Jun. 25, 1987

Related U.S. Application Data

[63] Continuation-in-part of Ser. No. 854,000, Apr. 21, 1986, Pat. No. 4,677,174, which is a continuation-in-part of Ser. No. 872,654, Jun. 10, 1986, Pat. No. 4,755,562.

[51] Int. Cl.⁴ ............... C08F 8/30; C08F 8/32; C08F 2/00
[52] U.S. Cl. .................... 525/274; 264/140; 264/144; 525/329.9; 525/285; 526/203
[58] Field of Search ........ 526/203; 525/329.9, 525/285, 274; 528/492; 264/140, 144

[56] References Cited

U.S. PATENT DOCUMENTS

| | | | |
|---|---|---|---|
| 2,984,639 | 5/1961 | Stamberger et al. | 525/329.9 |
| 3,008,851 | 11/1961 | Shimizu et al. | 525/374 |
| 3,015,653 | 1/1962 | Richards et al. | 526/203 |
| 3,444,151 | 5/1969 | Nerdol et al. | 526/203 |
| 4,525,527 | 6/1985 | Takeda et al. | 524/831 |
| 4,552,938 | 11/1985 | Makita et al. | 526/240 |
| 4,587,308 | 5/1986 | Makita et al. | 525/374 |

Primary Examiner—Joseph L. Schofer
Assistant Examiner—Peter F. Kulkosky
Attorney, Agent, or Firm—Mason, Kolehmainen, Rathburn & Wyss

[57] ABSTRACT

Improved water-absorbing, crosslinked acrylate resins are prepared by aqueous polymerization of (A) acrylic acid neutralized 70 to 100 mole percent for example with ammonia and/or caustic alkali and/or an amine; with (B) acrylamide in a mole ratio of 70 to 100 mole percent (A) to 30:0 mole percent (B); and (C) a water miscible or a water soluble polyvinyl monomer in the presence of (D) a styrene-maleic anhydride copolymer, neutralized 70 to 100 mole percent for example with ammonia, and/or caustic alkali and/or an amine, in an amount of 1% to 25% based on the weight of acrylic acid or acrylate, such that the amount of (C) is 0.001 to 0.6 weight percent based on the total weight of (A), (B), (C) and (D). In addition, surface treating the water-absorbing crosslinked acrylate resins with a polyquaternary amine substantially further increases both the rate of water absorption and the quantity of water absorbed and retained by the resin. The untreated and the surface-treated resins also maintain the necessary "dry feel" required for most applications.

41 Claims, 7 Drawing Sheets

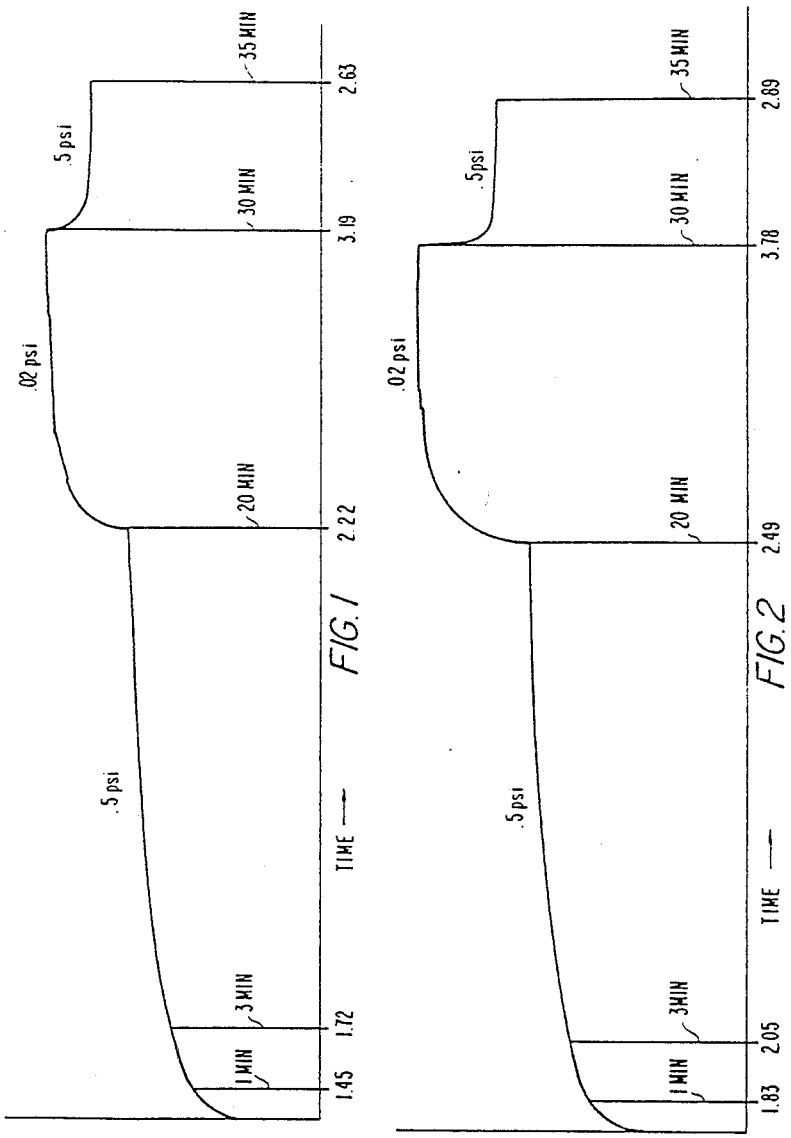

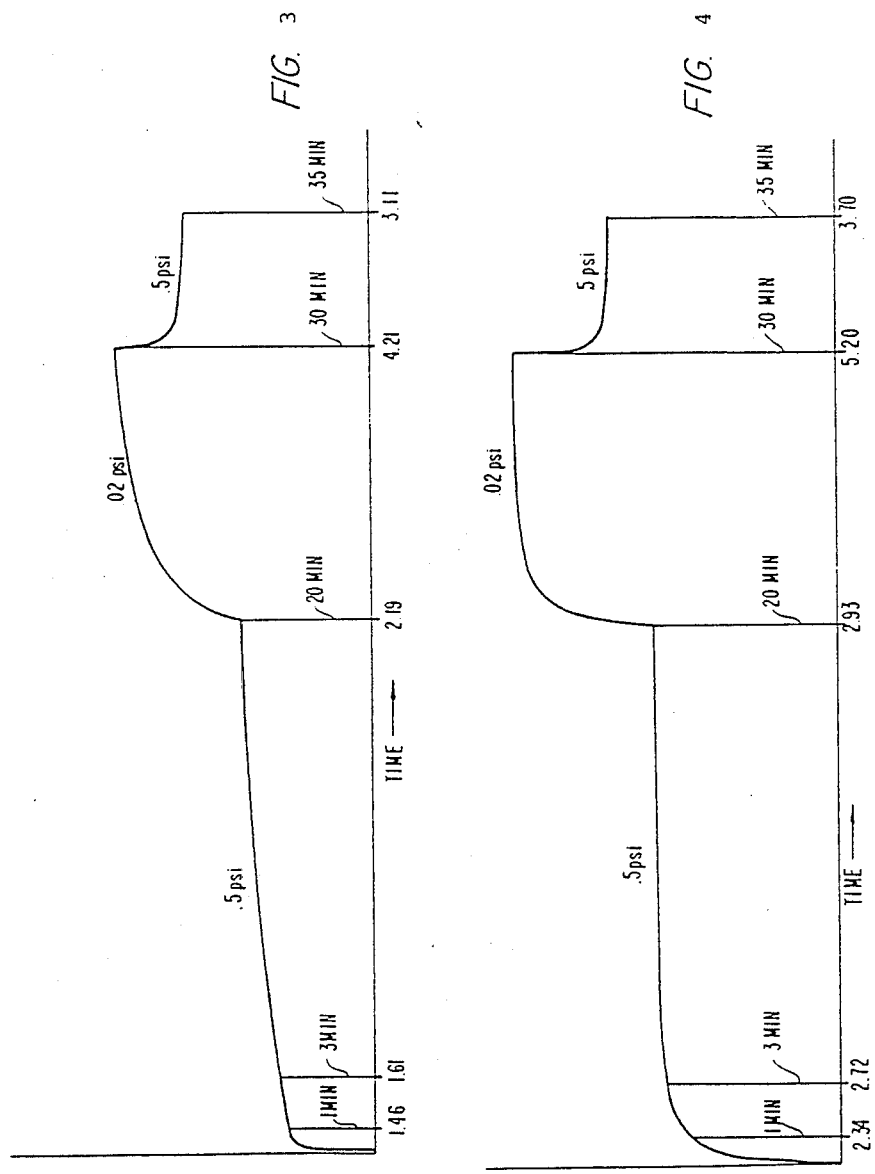

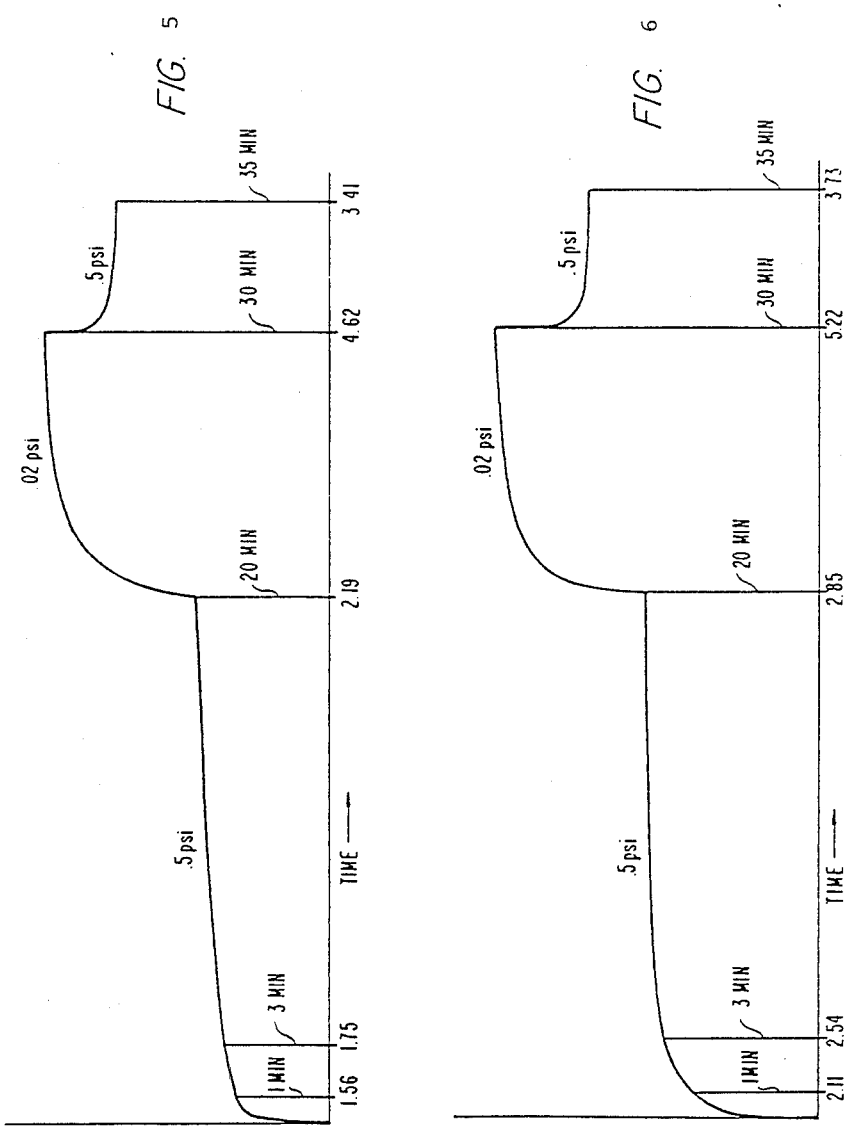

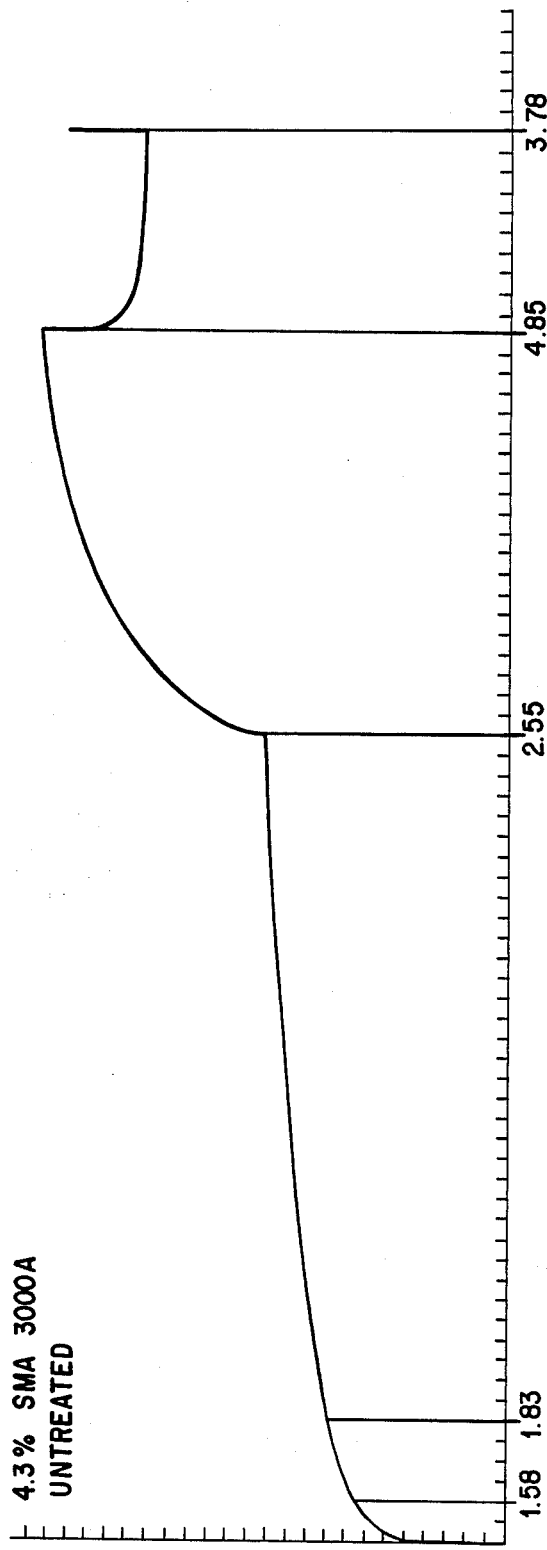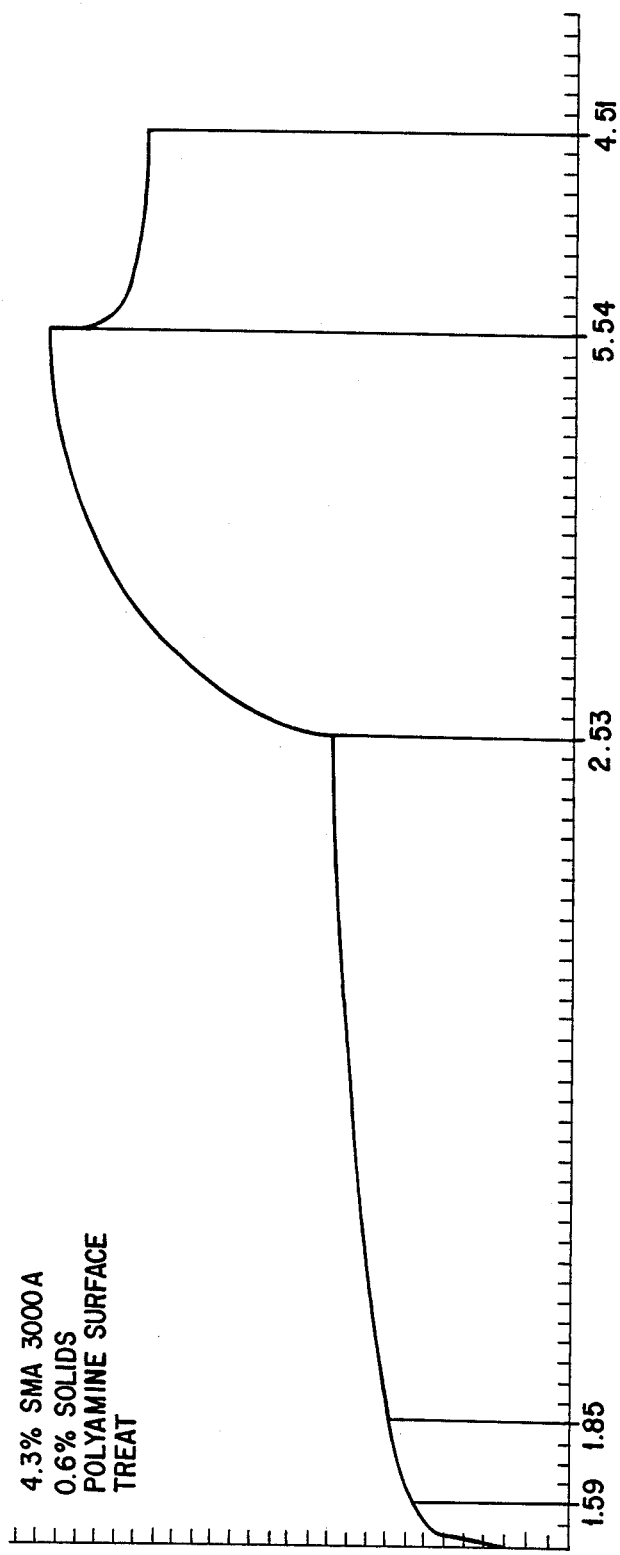

WATER ABSORBENT RESINS PREPARED BY POLYMERIZATION IN THE PRESENCE OF STYRENE-MALEIC ANHYDRIDE COPOLYMERS

CROSS-REFERENCE TO RELATED APPLICATION

This application is a continuation-in-part of my co-pending applications, Ser. No. 854,000, filed on April 21, 1986 and now issued as U.S. Pat. No. 4,677,174 and Ser. No. 872,654, filed on June 10, 1986 and now issued as U.S. Pat. No. 4,755,562.

FIELD OF THE INVENTION

The present invention relates to a method of manufacturing water-absorbent resins having improved water-absorbing and water-retaining properties and more particularly to a process of preparing crosslinked homopolymers and copolymers of acrylic acid in the presence of styrene-maleic anhydride resins. In addition, the present invention relates to a method of surface treating a water-absorbent resin, such as a neutralized, crosslinked, homopolymer or copolymer of acrylic acid including a styrene-maleic anhydride resin, with a polyquarternary amine to improve the water absorption and water retention properties of the resin.

BACKGROUND OF THE INVENTION

Water-absorbing resins have found wide use in sanitary goods, hygenic goods, water retaining agents, dehydrating agents, sludge coagulants, thickening agents, condensation preventing agents and release control agents for various chemicals. Water-absorbing resins are available in a variety of chemical forms including substituted and unsubstituted natural and synthetic polymers such as hydrolysis products of starch-acrylonitrile graft polymers, carboxymethylcellulose, crosslinked polyacrylates, sulfonated polystyrenes, hydrolyzed polyacrylamides, polyvinyl alcohols, polyethylene oxides, polyvinylpyrrolidines and polyacrylonitriles.

Each type of water-absorbing resin differs in ease and cost of manufacture, chemical and physical properties, rate of water-absorption, and degree of water-absorption and retention. For example, the hydrolysis products of starch-acrylonitrile graft polymers have a comparatively high ability to absorb water, but require a cumbersome process for production and have the disadvantages of low heat resistance and decaying or decomposing easily due to the presence of starch. Conversely, other water-absorbent polymers are easily and cheaply manufactured and are not subject to decomposition, but do not absorb liquids as well as the starch-acrylonitrile graft polymers.

Therefore, it would be extremely advantageous to provide a method of increasing the water absorption properties of a stable, easy to manufacture waterabsorbing resin to match the superior water-absorption properties of a difficult to manufacture polymer. Likewise, it would be advantageous to increase the liquid absorption properties of an already superior water-absorbent resin.

One of the processes for polymerizing acrylic acid and acrylates is aqueous solution polymerization. The polymer obtained by this process is soluble in water and, therefore, is crosslinked to modify the polymer into a useful water-absorbing resin. However, even if the modification is effected by reacting a crosslinking agent concurrently with or after aqueous solution polymerization, the resulting reaction product is in the form of a difficult to handle, highly viscous aqueous solution, or a gel, containing absorbed water. As a result, the aqueous solution or gel must be dehydrated (dried) to obtain a water-absorbing resin in the desired solid or powder form. However, it is difficult to dry the reaction product efficiently by the usual rotary drum roller method or spray drying method because care must be taken to avoid the excessive crosslinking that results from overheating during drying. Furthermore, insufficient drying of the resin results in reduced crosslinking density. Therefore, extreme difficulties are encountered in preparing a resin having a desired low water content and good water-absorbing ability.

Any method of improving the water-absorbing properties of a resin must also retain the "dry feel" of the resin after liquid absorption. Although water and liquid absorption is the primary function of the water-absorbing resin, in many applications it is almost equally important that the polymer maintain its "dry feel". The polymer must be able to absorb amounts of water several times its weight, plus be sufficiently crosslinked to avoid partial solubilization of the polymer to form a gel and lead to a slippery, wet feeling. Presently, water-absorbing resins, such as crosslinked polyacrylic acid, do possess a "dry feel" after significant water absorption. Thus any methods directed to improving the water-absorbing properties of such a resin should not alter the basic "dry feel" of the resin after liquid absorption.

Any method that both increases the water-absorbing capabilities of a water-absorbent resin and maintains the basic "dry feel" of the resin would enhance and broaden the application possibilities of many water-absorbent polymers. Such a method should be simple and economical to avoid increases in the raw material or the manufacturing cost of the water-absorbent resin.

SUMMARY OF THE INVENTION

In brief, the present invention is directed to a process for preparing improved water-absorbent crosslinked resins, of low water content, by aqueous solution polymerization without any additional dehydrating or drying step. The present invention also is directed to a method of surface treating a water-absorbent resin with a sufficient amount of polyquaternary amine to substantially improve the water-absorbent and water retention properties of the resin. It has been found that the surface treatment can be applied to a dried polymer at any time, either immediately prior to using the polymer or by incorporating the treatment into a manufacturing step immediately following the polymerization reaction and polymer drying steps.

Another object of the present invention is to provide a process for preparing a crosslinked resin by the aqueous polymerization of partially or fully neutralized acrylic acid and a water-miscible to water soluble polyvinyl monomer in the presence of a partially or fully neutralized styrene-maleic anhydride resin, in a combined concentration of 30 to 80% by weight partially or fully neutralized acrylic acid and 1% to 25% styrene-maleic anhydride resin, based on the weight of acrylic acid.

Another object of the present invention is to provide a process for preparing a crosslinked resin by polymerization of acrylic acid neutralized 70–100 mole percent and a polyvinyl monomer in the presence of a 70–100 mole percent neutralized styrene-maleic anhydride resin, in proportions of 30 to 80% by weight partially or fully neutralized acrylic acid; 1 to 25% based on the weight of acrylic acid of styrene-maleic anhydride resin and 0% to 30% by weight acrylamide, based on the weight of acrylic acid, in aqueous solution.

Another object of the present invention is to provide a process for producing a water-absorbent resin crosslinked with 0.2 weight percent to 0.6 weight percent based on the weight of monomers, of a water miscible or water soluble polyvinyl monomer crosslinking agent to achieve a "dry feel" to the resin after significant water absorption.

Another object of the present invention is to provide a water-absorbent resin having improved water-absorption and water-retention properties by polymerizing the partially or completely neutralized acrylic acid in the presence of a partially or fully neutralized styrene-maleic anhydride resin.

Another object of the present invention to surface treat water-absorbent resins to substantially increase the water absorption and water retention properties of the polymer.

Another object of the present invention is to surface treat water-absorbent resins with a polyquaternary amine to substantially increase the water absorption and water retention properties of the resins.

Another object of the present invention is to provide a process for producing a polyacrylate resin copolymer crosslinked with 0.2 weight percent to 0.6 weight percent based on the weight of monomers, of a water miscible or water soluble polyvinyl monomer crosslinking agent and thereafter contacting the resin with a polyquaternary amine in an amount sufficient for interaction to substantially improve the water absorbency and water retention properties of the resin and to maintain a "dry feel" to the resin after significant water absorption.

In brief, the present invention is directed to a process for preparing water-absorbing, crosslinked resins by aqueous polymerization of (A) acrylic acid neutralized 70 to 100 mole percent for example with ammonia and-/or caustic alkali and/or an amine; with (B) acrylamide in a mole ratio of 70 to 100 mole percent (A) to 30:0 mole percent (B); and (C) a water miscible or a water soluble polyvinyl monomer; in the presence of (D) a styrene-maleic anhydride copolymer neutralized 70 to 100 mole percent for example within ammonia and/or caustic alkali and/or an amine, in an amount of 1% to 25% based on the weight of acrylic acid or acrylate, such that the amount of (C) is 0.001 to 0.6 weight percent based on the total weight of (A), (B), (C) and (D). To achieve the full advantage of the present invention the concentration of monomers (A), (B), (C) and of resin (D) is at least 50 wt. % of the aqueous solution. During synthesis, the resin dries to an acceptable water content of at least less than 15% by weight of the polymer, and thereafter the resin is contacted with a polyquaternary amine in an amount sufficient for interaction to substantially improve the water-absorbent and water retention properties of the resin. A "dry feel" is obtained at a polyvinyl monomer concentration of at least 0.2 wt. percent of the aqueous solution.

In accordance with an important embodiment of the present invention, a heated aqueous solution comprising (A) acrylic acid neutralized 70 to 100 mole percent for example with ammonia, and/or caustic alkali and/or an amine; and (B) styrene-maleic anhydride resin neutralized 70 to 100 mole percent, for example with ammonia and/or caustic alkali and/or an amine, in an amount of 1% to 25% based on the amount of acrylic acid and acrylate, computed as based on acrylic acid; and (C) a water-miscible to water-soluble polyvinyl monomer, water and, when desired, an organic solvent having a boiling point of 40° to 150° C., and having a styrene-maleic anhydride resin-monomer concentration of (A) plus (B) plus (C) of 30 to 80 wt. % is subjected to polymerization in the presence of one or more polymerization initiators without external heating while allowing water to evaporate off. After sufficient water has evaporated so that the resin has about 15% by weight water or less, the resin is contacted with a polyquaternary amine to substantially further increase the water absorbency and water retention properties of the polymer.

BRIEF DESCRIPTION OF THE DRAWINGS

The above and other objects and advantages of the present invention will become apparent from the following detailed description of the present invention taken in conjunction with the drawings, wherein:

FIG. 1 is a graph obtained using a gravimetric absorbency testing system (GATS) showing the water absorbency vs. time for an acrylic homopolymer.

FIG. 2 is a graph obtained using a gravimetric absorbency testing system (GATS) showing the water absorbency vs. time for the same acrylic homopolymer used to obtain FIG. 1 after surface treatment with 0.3% of a polyquaternary amine (by dry weight).

FIGS. 3 and 4 are GATS graphs showing water absorbency vs. time for an acrylic-styrene copolymer having 2% styrene without surface treatment and with surface treatment by 0.3% of a polyquaternary amine (by dry weight), respectively.

FIGS. 5 and 6 are GATS graphs showing water absorbency vs. time for an acrylic-styrene copolymer having 4% styrene without surface treatment and with surface treatment by 0.5% of a polyquaternary amine (by dry weight), respectively.

FIGS. 7 and 8 are GATS graphs showing water absorbency vs. time for an acrylate polymer including 4.3% styrene-maleic anhydride resin (3:1 ratio of styrene to maleic anhydride) without surface treatment and with surface treatment by 0.6% polyquaternary amine (by dry weight), respectively.

DETAILED DESCRIPTION OF THE INVENTION

Figure 9:
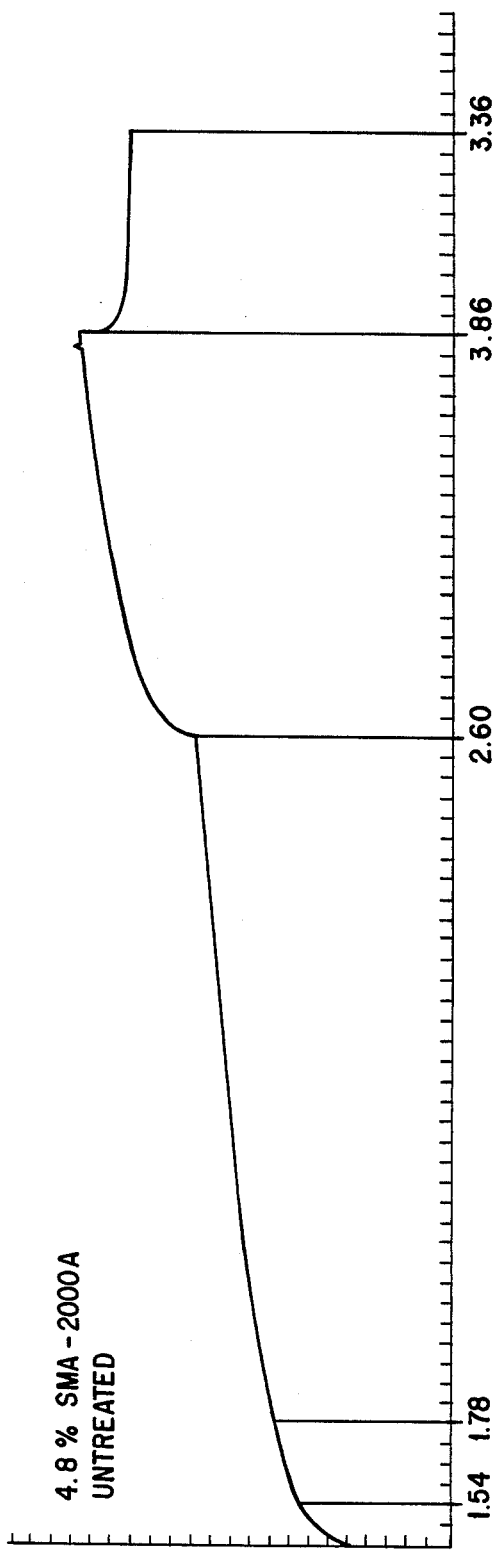
FIGS. 9 and 10 are GATS graphs showing water absorbency vs. time for an acrylate polymer including 4.8% styrene-maleic anhydride resin (2:1 ratio of styrene to maleic anhydride) without surface treatment and with surface treatment by 0.6% polyquaternary amine (by dry weight), respectively.
Figure 10:
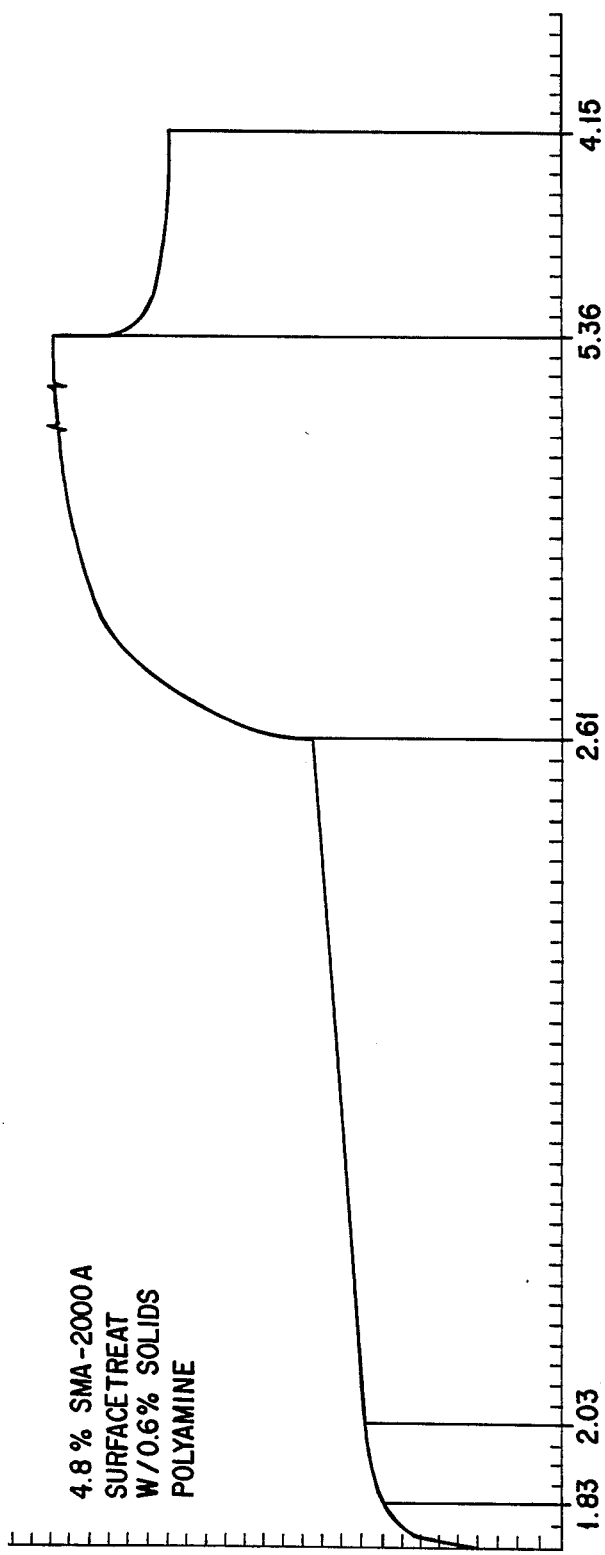
Figure 11:
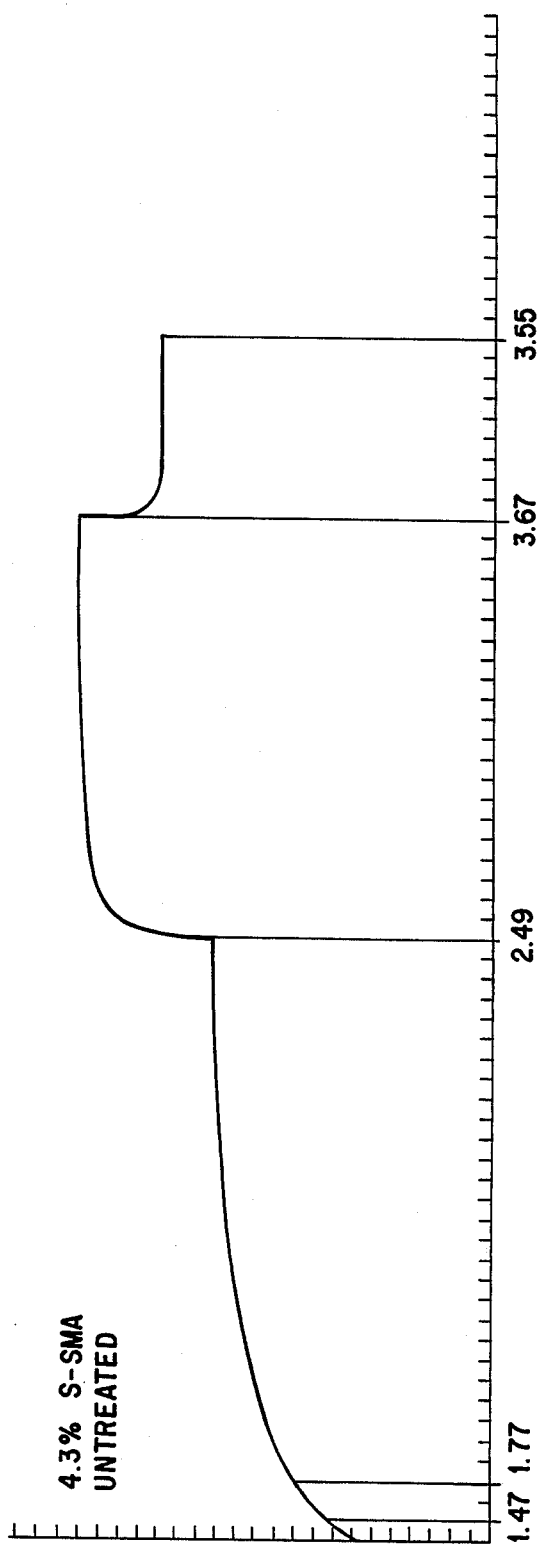
FIGS. 11 and 12 are GATS graphs showing water absorbency vs. time for an acylate polymer including 4.3% sulfonated styrene-maleic anhydride resin (3:1 ratio of styrene to maleic anhydride) without surface treatment and with surface treatment by 0.3% polyquaternary amine (by dry weight), respectively.
Figure 12:
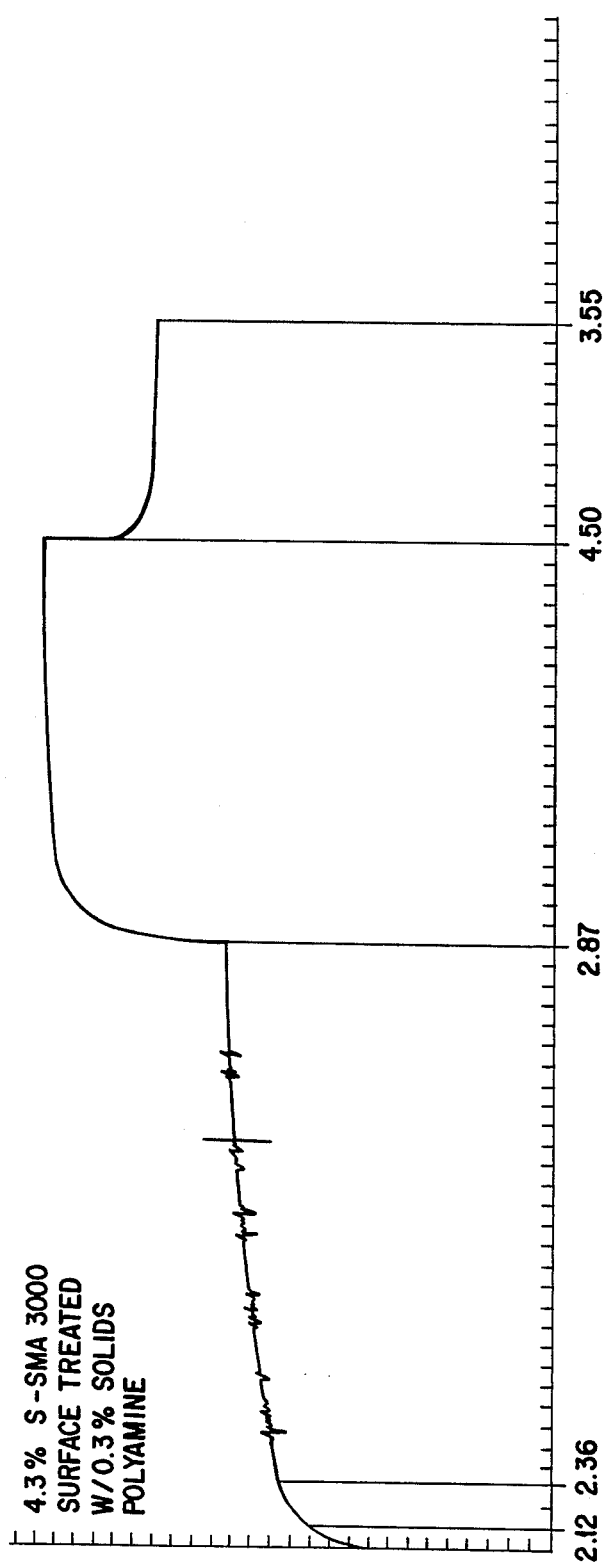

In accordance with the present invention, improved crosslinked water-absorbent resins are prepared by aqueous solution polymerization while dehydrating or drying the reaction product during polymerization by utilizing the exothermic heat from the copolymerization and crosslinking reactions for drying.

In accordance with another important feature the present invention, the water-absorbent resins are surface treated with polyquaternary amines to further substantially and unexpectedly increase the rate of water absorption, amount of water absorption and overall retention of water by the resin. Treatment of the polymer at any time after synthesis and sufficient drying will improve its water absorption properties; however, for economics and ease of manufacture, the surface treatment is most advantageously performed immediately after the polymer is synthesized, dried to an appropriate water content and sized, such as by grinding.

It has been found that acrylic acid, neutralized in the range of 70 to 100 mole percent, will polymerize in the presence of partially or fully neutralized styrene-maleic anhydride resins, and crosslink rapidly with a polyvinyl monomer crosslinking agent to drive away excess water leaving a solid, water-absorbing resin having a desired degree of polymerization as well as new and unexpected water-absorption and water-retention properties. One or more polymerization catalysts or initiators can be added to the aqueous monomer mixture to aid in polymerization. As will be discussed more fully hereinafter, subsequent surface treatment with an electrically positive-charged polyquaternary amine serves to further substantially improve the water-absorption and water-retention properties of the water-absorbent resin.

According to the present invention, a hot aqueous solution comprising acrylic acid neutralized 70 to 100 mole percent; a styrene-maleic anhydride resin neutralized 70 to 100 mole percent; a water-miscible or water-soluble polyvinyl monomer; water and, when desired, an organic solvent having a boiling point of 40° to 150° C., and that contains the acrylate monomer; styrene-maleic anhydride resin; and the polyvinyl monomer in a combined concentration of 30 to 80 wt.%, is prepared.

To achieve the full advantage of the present invention, the acrylate, styrene-maleic anhydride resin, and polyvinyl monomers are present in a combined concentration of less that 70 weight percent of the solution. In accordance with another important embodiment of the present invention, the combined concentration of the acrylate, styrene-maleic anhydride resin and polyvinyl monomers is less than 55 weight percent of the solution. The concentration of the monomers and styrene-maleic anhydride resin is deliberately determined considering the state of the solution (i.e., as to whether or not the monomers can be completely dissolved in water), ease of the reaction of the monomers, escape of the monomers due to the scattering during the reaction, and similar process parameters.

The aqueous solution can be prepared easily usually by placing acrylic acid, a styrene-maleic anhydride resin, a strong alkali such as potassium hydroxide and/or ammonium hydroxide or a basic amine for neutralizing the acid and resin, and the polyvinyl monomer into water in such amounts that the resulting solution has the above-mentioned monomer and styrenemaleic anhydride resin concentration. To thoroughly mix the monomers and the resin, the mixture can be heated to an elevated temperature.

Any strongly basic alkali metal compound can be used for neutralization of the acrylic acid, such as ammoniun hydroxide, potassium hydroxide, sodium hydroxide, lithium hydroxide, cesium hydroxide, ammonium carbonate, potassium carbonate and/or sodium carbonate. Although it is desirable to use the neutralizing agent usually in an amount sufficient to neutralize acrylic acid 100 mole %, it is not necessary to neutralize the acid 100%. However, the neutralizing agent, e.g., hydroxide, is used in such an amount as to achieve not less than about 70% neutralization. Accordingly, the aqueous solution may contain up to about 30 mole percent of free acrylic acid based on the amount of acrylic acid and acrylate. However, a large quantity of free acrylic acid, if present in the aqueous solution, is likely to partly splash out of the reaction vessel, resulting in a loss during the reaction, leading to a reduced degree of polymerization. Using an excessive amount of neutralizing agent will not pose any particular problem, however, the excess neutralizing agent does not participate in the polymerization reaction and is therefore useless.

It also has been found that when the aqueous solution further contains an organic solvent having a boiling point of about 40° to about 150° C., the temperature of the aqueous solution is controlled much more easily, and the resulting crosslinked water-absorbent polymer has a remarkably improved ability to absorb water at an initial rate.

In accordance with the present invention, when incorporating an organic solvent, the aqueous solution has a solidifying point of about 10° to about 20° C. lower than solutions absent the organic solvent. Therefore, the allowable range of temperature control is increased by at least about 3 times. The organic solvent is vigorously evaporated together with water by the heat of polymerization of the monomers. Since the latent heat of the evaporation of the organic solvent is considerably smaller than that of water, the organic solvent functions as a blowing agent in the polymerization reaction system, consequently rendering the resulting water-absorbent resin porous. The resin therefore exhibits about 2 to about 5 times higher initial rate of water-absorption than the one obtained without using the organic solvent while possessing high water-absorbing ability. Thus, the organic solvent, when added to the aqueous monomer solution, produces improved effects without in any way impairing the advantages resulting from the use of the monomer solution.

Examples of organic solvents that can be used in the invention when desired have a boiling point of about 40° to about 150° C., and include methanol, ethanol, propanol and similar alcohol solvents; acetone, methyl ethyl ketone and similar ketone solvents; cyclohexane, n-hexane, n-heptane and like hydrocarbon solvents; benzene, toluene and like aromatic hydrocarbon solvents; and tetrahydrofuran and like furan solvents. These solvents may be used singly or in admixture. The solvent is used in an amount of 0.5 to 15 wt. %, preferably 1 to 10 wt. %, based on the combined amount of the acrylic acid, styrene-maleic anhydride resins and polyvinyl monomers. With less than 0.5 wt. % of the solvent present, a sufficient blowing action will not occur, and the solidifying point of the monomer solution will not be greatly lowered. Conversely, if more than 15 wt. % of the solvent is used, the resulting resin is likely to exhibit reduced water-absorbing ability, although achieving a high initial rate of water-absorption. Moreover the monomers are likely to separate out from the aqueous solution and therefor affect polymerization. Since the monomer solution is heated prior to polymerization, and because the organic solvent evaporates along with water, the boiling point of the solvent is more preferably in the range of 55° to 120° C.

In accordance with the present invention, acrylic acid, neutralized 70-100 mole percent, is mixed with 1% to 25%, based on the weight of acrylic acid, styrene-maleic anhydride resin, neutralized to 70-100 mole percent; and a water-miscible or water-soluble polyvinyl monomer in an aqueous solution at a temperature of about 20° to 100° C. The solution is subjected to a polymerization reaction and a crosslinking reaction by the addition of a polymerization initiator. The polymerization reaction proceeds sufficiently within a very short period of time and if the monomer concentration is at least 30 percent by weight of the aqueous monomer mixture, the heat of the polymerization and crosslinking reactions will evaporate water rapidly from the reaction system to form a dry, solid (less than 15 percent by weight water), water-absorbent resin without the need for any subsequent drying step. The solid can be easily pulverized into a powder suitable for any desired use.

According to an important embodiment of the present invention, a hot, i.e., at least 25° C., aqueous solution is prepared first including acrylic acid neutralized 70 to 100 mole percent; styrene-maleic anhydride resin neutralized 70 to 100 mole percent in an amount of 1% to 25% based on the weight of acrylic acid; optionally acrylamide; a water-miscible or water-soluble polyvinyl monomer; and water. The aqueous solution can be prepared easily by placing (A) acrylic acid, and an amine and/or a caustic alkali and/or ammonia for neutralizing the acid; (B) styrene-maleic anhydride resin, in an amount of 1% to 25% based on the weight of acrylic acid, and an amine and/or a caustic alkali and/or ammonia for neutraling the resin; (C) acrylamide (0-30 mole percent based on acrylic acid); and (D) a polyvinyl monomer into water to form a mixed monomer solution. To dissolve the monomers thoroughly, the mixture can be heated to an elevated temperature up to the boiling point of water, i.e., 100° C.

The polyvinyl monomer to be used in accordance with the present invention should be miscible with or soluble in water so that the monomer will be uniformly dissolved or dispersed in the aqueous solution of the monomer mixture. Examples of such polyvinyl monomers include trimethylolpropane triacrylate, bisacrylamides such as N,N'-methylenebisacrylamide and N,N'-methylenebismethacrylamide; polyacrylic (or polymethacrylic) acid esters represented by the following formula (I); and diacrylamides represented by the following formula (II). Among these, especially preferably are N,N'-methylenebisacrylamide, N,N'-methylenebismethacrylamide and like bisacrylamides.

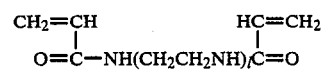

Formula (I)

wherein X is ethylene, propylene, trimethylene, hexamethylene, 2-hydroxypropylene

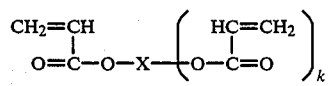

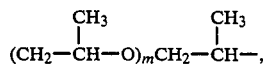

n and m are each an integer of from 5 to 40, and k is 1 or 2.

The compounds of the forumula (I) are prepared by reacting polyols, such as ethylene glycol, propylene glycol, trimethylolpropane, 1,6-hexanediol, glycerin, pentaerythritol, polyethylene glycol and polypropylene glycol, with acrylic acid or methacrylic acid.

$$\begin{array}{cc} CH_2=CH & HC=CH_2 \\ | & | \\ O=C-NH(CH_2CH_2NH)_l C=O \end{array}$$ Formula(II)

wherein l is 2 or 3.

The compounds of the formula (II) are obtained by reacting polyalkylenepolyamines, such as diethylenetriamine and triethylenetetramine, with acrylic acid.

The polyvinyl monomer is used in an amount of about 0.001 to 0.6 wt. % based on the amount of acrylic acid, acrylamide monomers and styrene-maleic anhydride resin in the aqueous monomer mixture. In accordance with an important embodiment of the present invention, the polyvinyl monomer crosslinking agent should be present in the aqueous solution in an amount of at least 0.2 wt. % based on the total weight of monomers and styrene-maleic anhydride resin to provide a resin sufficiently crosslinked to have a "dry feel" after significant water-absorption. If the polyvinyl monomer is included in the aqueous solution in an amount of 0.2 to 0.6 weight percent based on the weight of neutralized acrylic acid, neutralized styrene-maleic anhydride resin and polyvinyl monomers, the resulting polymer will have an exceedingly "dry feel" on absorption of water.

The styrene-maleic anhydride resin used in accordance with the present invention is initially insoluble in water, however after a sufficient amount of an alkaline substance, such as a hydroxide, like sodium hydroxide, potassium hydroxide, ammonium hydroxide, lithium hydroxide, or cesium hydroxide; a carbonate, like sodium carbonate, potassium carbonate or ammonium carbonate; or an amine is added to the aqueous solution containing the acrylic acid, polyvinyl monomer and styrene-maleic anhydride resin, the sty- rene-maleic anhydride is soluble in water. The sty- rene-maleic anhydride resin does not copolymerize with the neutralized acrylic acid and polyvinyl monomer; however, the styrene-maleic anhydride monomer is physically entangled and included, essentially non-covalently, throughout the crosslinked acrylate polymer, and surprisingly and unexpectedly results in improved water-absorption and improved water-retention by the polyacrylate polymer.

The styrene-maleic anhydride resins that are useful in the present invention are low molecular weight resins having the following formula in the unneutralized form:

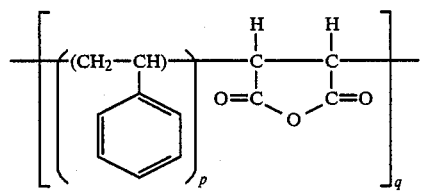

wherein p=1-3 and q=6-8. However, modified styrene-maleic anhydride resins, such as resins that are partially esterfied or resins containing sulfonate groups on the benzene ring, also can be used according to the method of the present invention. From the generalized formula for the styrene-maleic anhydride resin, it can be seen that resins have a weight average molecular weight from about 1500 to about 2000 and that the ratio of styrene-to-maleic anhydride can vary from 1:1 to 3:1, with the resin having a 3:1 styrene-to-maleic anhydride ratio exhibiting the lowest water-solubility. In accordance with the method of the present invention, suitable styrene-maleic anhydride resins are exemplified by the following tradename products:

SMA 1000,
SMA 2000,
SMA 3000,
SMA 2625,
SMA 17352,
S—SMA 1000,
S—SMA 3000,
SMA 1000-A,
SMA 2000-A,
SMA 3000-A,
SMA 1440, and
SMA 1440H, all available from Arco Chemical Co.

It has been found that the particular styrene-maleic anhydride resin used to improve the water-absorption and water-retention properties of the acrylate polymers may vary according to the particular alkali that is used to neutralize the acrylic acid and styrene-maleic anhydride resin. For example, if a potassium-based alkali is used to neutralize the acylic acid and styrene-maleic anhydride resin, a 3:1 ratio of styrene to maleic anhydride in the styrene-maleic anhydride resin exhibits the most improved water-absorption and water-retention properties. However, if an ammonium-based alkali is used, a 1:1 ratio of styrene to maleic anhydride in the styrene-maleic anhydride resin exhibits the most improved water-absorption and water-retention properties.

The styrene-maleic anhydride resin improves the water-absorption and water-retention of the polyacrylate polymer when the styrene-maleic anhydride resin is present from about 1% to about 25%, based upon the weight of acrylic acid and acrylate (computed based on the molecular weight of acrylic acid). To achieve the full advantage of the present invention, the styrene-maleic anhydride ratio is present from about 2% to about 12% based upon the weight of the acrylic acid and acrylate (computed based on the molecular weight of acrylic acid).

According to the method of the present invention, the aqueous mixed monomer and styrene-maleic anhydride resin solution is heated and thereafter subjected to polymerization and crosslinking reactions with the addition of a polymerization initiator. Although the temperature of the aqueous mixed monomer and resin solution is not particularly limited since the polymerization of the monomers in solution is initiated by the addition of the initiator, the temperature is usually about 50° to about 85° C., preferably about 60° to about 75° C.

Various polymerization initiators that are known for use in preparing polyacrylates, can be used. Examples of useful initiators are redox initiators comprising a reducing agent, such as a sulfite or bisulfite of an alkali metal, ammonium sulfite, ammonium metabisulfate or ammonium bisulfite, a persulfate of an alkali metal or ammonium persulfate; t-butyl hydroperoxide; di-t-butyl hydroperoxide; t-butyl perbenzoate; t-butyl peroxy isopropyl carbonate; and peroxy-3,3,5 trimethylcyclohexane. Examples of suitable thermal initiators include azobisisobutyronitrile; 4-t-butylazo-4'-cyanovaleric acid; 4,4'-azobis(4-cyanovaleric acid); 2,2'-azobis(2-amidinopropane)dihydrochloride; 2,2'-azobis(2,4-dimethylvaleronitrile); dimethyl 2,2'-azobisisobutyrate; 2,2'-azodimethyl bis(2,4-dimethylvaleronitrile); (1-phenylethyl)azodiphenylmethane; 2,2'-azobis(2-methylbutyronitrile); 1,1'-azobis(1-cyclohexanecarbonitrile); 2-(carbamoylazo)-isobutyronitrile; 2,2'-azobis(2,4,4-trimethylpenta 2-phenylazo-2,4-dimethyl-4-methoxyvaleronitrile; 2,2'-azobis(2-methylpropane); 2,2'-azobis(N,N'dimethyleneisobutyramidine)dihydrochloride; 4,4'azobis(4-cyanopentanoic acid); 2,2'-azobis(2-methyl-N-[1,1-bis(hydroxymethyl)-2-hydroxyethyl] propionamide); 2,2'-azobis(2-methyl-N-[1,1-bis(hydroxymethyl)ethyl]propionamide); 2,2'-azobis[2-methyl-N(2-hydroxyethyl)propionamide]; 2,2'-azobis-(isobutyramide)dihydrate and the like.

These initiators, redox and thermal, can be used singly or in a suitable combination. Of these, especially preferable are a redox initiator composed of ammonium persulfate and sodium hydrogen sulfite, and azo initiators such as azobisisobutyronitrile and 2,2'-azobis(2-amidinopropane)dihydrochloride. The initiators are advantageously used usually in the form of an aqueous solution, but can be used as diluted with a suitable solvent. The initiator is used in a usual amount, i.e., in an amount, calculated as solids, of about 0.1 to about 10%, preferably about 0.5 to about 5%, of the combined weight of the monomers, namely acrylate (and free acrylic acid); acrylamide; styrene-maleic anhydride resin; and polyvinyl monomer crosslinking agent. Depending on the amount and kind of the initiator, the initiator is usable together with isopropyl alcohol, alkyl mercaptan or other chain transfer agents to control the molecular weight of the polyacrylate copolymer to be obtained.

When a thermal and redox initiator are used in combination, the temperature of the monomer and styrene-maleic anhydride solution can vary considerably in accordance with the process of the present invention prior to the addition of the thermal and redox initiators, depending upon the particular thermal initiator added. In any event, the initial temperature of the monomer solution should be below the thermal decomposition temperature of the initiator or substantial polymerization initiation results; and the temperature of the monomer solution should be high enough that the redox initiator causes sufficient polymerization at the initial temperature of the monomer solution to raise the temperature of the mixed monomer solution to a level sufficient that the thermal initiator, together with the redox initiator, causes substantially complete polymerization leaving less than about 1000 PPM free monomer, and generally less than about 500 PPM free monomer. Free monomer levels less than 200 PPM and even less than 100 PPM have been achieved in accordance with the process of the present invention. The combination of initiators can be added to the mixed monomer solution in a batch process or continuously.

In accordance with an important feature of the present invention, it has been found that a combination of at least one thermal initiator with at least one redox initiator enables efficient polymerization while limiting the free acrylic acid and acrylate monomer content to less than 1000 ppm, and generally less than 500 PPM in the completed water-absorbing polymer.

By the addition of the polymerization initiator, the monomer solution is subjected to polymerization with evaporation of water without heating the system from outside. More advantageously, the reaction is carried out by admixing a predetermined amount of the initiator or an aqueous solution thereof with the mixed monomer/styrene-maleic anhydride resin solution and causing the resulting mixture to flow down onto and spread over a traveling conveyor belt or reacted continuously. The initiator can be added to the mixed monomer-resin solution as it is poured onto the conveyor belt.

The copolymerization proceeds rapidly after admixing the initiator with the mixed monomer-resin solution and is completed within a short period of time, usually in about 30 seconds to about 10 minutes. The reaction is exothermic, so that the reaction system is rapidly heated to about 100° to about 130° C. by the heat of polymerization. Consequently, particularly where the monomer concentration in the mixed solution is at least 50 percent by weight, the water evaporates from the system rapidly to give a relatively dry, solid copolymer of low water content without resorting to any external heating. The water content of the copolymer is usually up to about 15%, and generally about 8 to 12% by weight as recovered. Subsequently, the dry solid copolymer can be made into the desired powder easily by a usual method, for example by pulverization, without a drying step.

The powder thus obtained has outstanding water-absorbing ability and is useful for sanitary goods, paper diapers, disposable diapers and like hygenic goods, agricultural or horticultural waterretaining agents, industrial dehydrating agents, sludge coagulants, thickening agents, condensation preventing agents for building materials, release control agents for chemicals and various other applications.

In accordance with another important feature of the present invention, it has been found that surface treatment of the water-absorbent resin with a polyquaternary amine further substantially and unexpectedly increases the water-absorbent qualities of the resin while retaining the necessary "dry feel" of the resin. In a preferred method, the polyquaternary amine surface treatment is performed immediately following the polymerization, drying and sizing steps. To achieve the full advantage of the present invention, the polyquaternary amine is dispersed in a suitable solvent to produce a solution containing 0.1% to 20% polyquaternary amine by weight. Suitable solvents include liquids capable of solubilizing the polyquaternary amine and of rapid and complete evaporation. Such solvents include the lower alcohols, especially methanol or isopropyl alcohol; lower ketones, such as acetone or methyl ethyl ketone; and other such low molecular weight organic solvents. Water is not a recommended solvent due to its low evaporation rate and its absorption by the water-absorbent resin, while methanol has been found to be the most advantageous polyquaternary amine diluent.

The polyquaternary amine-methanol solution is evenly sprayed onto the surface of the water-absorbent resin, followed by a blending operation to attain a uniform coating of the polyquaternary amine on the surface of the polymer. After blending and methanol evaporation, the water-absorbent resin is thereby surface coated with 0.1% to 5.0% (by dry weight) of a polyquaternary amine. It is not essential to treat the water-absorbent resin immediately after synthesis and drying, since surface treatment of the water-absorbent polymer at any time prior to use will yield the new and unexpected results described herein.

Polyquaternary amines are readily available products from a number of commercial sources. The actual chemical structure of the polyquaternary amine will depend upon the starting materials used to synthesize the polyquaternary amine, with the diversity of available starting materials leading to polyquaternary amines of quite diverse structure. Among the various polyquaternary amines available are condensation products of hexamethylenediamine, dimethylamine, and epichlorohydrin; condensation products of dimethylamine and epichlorohydrin; copolymers of hydroxyethyl cellulose and diallyldimethyl ammonium chloride; copolymers trimethyl ammonium chloride; hydroxyethyl cellulose reacted with epichlorohydrin, then quaternized with trimethylamine; or homopolymers of diallyldimethyl ammonium chloride. Polyquaternary amines may also be synthesized by the reaction of dimethyl sulfate with polymers such as polyethyleneimines, copolymers of vinyl pyrrolidone and dimethylaminoethyl methacrylate, or copolymers of ethyl methacrylate, abietyl methacrylate and diethylaminoethyl methacrylate. Regardless of the overall chemical structure, each of the polyquaternary amines possesses the positively-charged ammonium nitrogen atom required for interaction with the negatively-charged moiety of the water-absorbent polymer.

The polyquaternary amines are available in a wide molecular weight range, however, for the present invention the preferred molecular weight of the polyquaternary amine ranges from about 200 to about 5000. To achieve the full advantage of the present invention, the molecular weight range of the polyquaternary amine is between about 300 and about 4000. Suitable polyquaternary amines are exemplified by the following tradename products:
MAGNIFLOC 577C from American Cyanamid Co.;
MAGNIFLOC 579C from American Cyanamid Co.;
MAGNIFLOC 581C from American Cyanamid Co.;
MIRAPOL WT from National Chemical Co., Inc.;
RETEN 205 from Hercules, Inc.;
RETEN 210 from Hercules, Inc.;
RETEN 220 from Hercules, Inc.;
UCARE Polymer JR-30M from Union Carbide Corp.;
UCARE Polymer JR-125 from Union Carbide Corp.;
GAFQUAT 734 from GAF Corp.; and
GAFQUAT 755 from GAF Corp.
However, other polyquaternaries can be used in the present invention.

In accordance with a new and unexpected feature of the present invention, it has been found that by polymerizing partially neutralized or fully neutralized acrylic acid in the presence of a fully or partially neutralized styrene-maleic anhydride resin, the total absorbency of the resulting polymer as well as the retention capacity of the polymer is unexpectedly superior to the absorbent polymer made without the styrene-maleic anhydride resin. Further, in accordance with another new and unexpected feature of the present invention, when the styrene-maleic anhydride resin is neutralized and is included in the monomer solution in an amount of 1-25% based on the weight of acrylic acid and acrylate (computed based on the molecular weight of acrylic acid), the initial rate of the water-absorption of the resulting copolymer is unexpectedly superior to the acrylate polymer manufactured absent the styrene-maleic anhydride resin. It is seen that adding the styrene-maleic anhydride resin to the monomer solution in an amount of about 1% to about 5% based on the weight of acrylic acid, only increases the total water-absorption and total water retention of the polymer. However, when the styrene-maleic anhydride resin is added to the mixed monomer solution in amount of about 5% to about 25% based on the weight of acrylic acid, not only is the total water-absorption and the total water retention far superior to that of the polymer alone, but the initial rate of water-absorption is far superior to that of the acrylic homopolymer and to that of the acrylic acid acrylamide copolymer. Unexpectedly, the total water-absorption and the total water-retention is further increased when the polymer including the styrene-maleic anhydride resin is surface treated with a polyquarternary amine.

In order to show the new and unexpected results achieved by the polymerization of partially or fully neutralized acrylic acid in the presence of a styrene-maleic anhydride resin, the water-absorption and retention properties of an acrylic acid homopolymer was studied, as shown in FIG. 1. The acrylate crosslinked polymer was prepared, and surface treated, in the same manner as described with respect to Example 1 using the following mixed monomer solution:

| CHEMICAL | PARTS BY WEIGHT | PERCENT |
|---|---|---|
| Acrylic Acid | 16.80 | 54.15 |
| Ammonium hydroxide (30% aqueous ammonia) | 4.20 | 13.54 |
| Potassium hydroxide | 4.20 | 13.54 |
| Azo crosslinking agent | 0.13 | 0.42 |
| GPTA (glycerol propoxy triacrylate molecular weight 428.5) | 0.002 | 0.01 |
| Ammonium carbonate | 3.31 | 10.67 |
| Water | 2.30 | 7.67 |
| TOTAL | 30.94 | 100.00 |

To demonstrate the new and unexpected results achieved by surface treating partially or fully neutralized homopolymers of acrylic acid or copolymers of acrylic acid with acrylamide, and styrene-maleic anhydride resin, both untreated and surface-treated with a polyquarternary amine, attention is directed to FIGS. 1 through 14. Each acrylate polymer was synthesized in the presence of a styrene-maleic anhydride resin and in the same manner as described above for the crosslinked polymer of acrylic acid. In each case, the polymer was tested in its untreated form, or first treated with a polyquaternary amine before testing.

The results shown in FIGS. 1 through 14 were obtained using a gravometric absorbency testing system (GATS). The polymer made in accordance with Example 1 and using the mixed monomer solution listed above is placed in contact with water under a retaining disc exerting 0.5 psi pressure on the polymer for 20 minutes to determine an initial rate of warer-absorption and, after 20 minutes, the pressure above the polymer is reduced to 0.02 psi with a lighter retaining disc for 10 minutes to determine a total water-absorption. At a 30 minute time interval, the pressure above the polymer is again increased to 0.5 psi to determine a total amount of water retained by the polymer. Water-absorption readings determined by increase in polymer rate were taken at the 1 and 3 minute time periods to determine an initial rate of water-absorption. A reading was taken at the 20 minute time interval to determine the total water-absorbed under the 0.5 psi retaining disc and water-absorption readings taken at the 30 minute time interval to determine the total water-absorbed by the polymer. Readings taken at a 35 minute time interval with the 0.5 psi retaining weight on the polymer were taken to determine the total amount of water retained by the polymer. The readings on the lower coordinate, or x axis of the graph of FIG. 1 represent the grams of water-absorbed per 0.1 gram of polymer and are as follows: 1 minute, 1.45; 3 minutes 1.72; 20 minutes, 2.22; 30 minutes, 3.19, 35 minutes, 2.63.

Referring to FIG. 2, the same procedure was used to determine the initial water absorbency, total water absorbency and total water retention of the same homopolymer tested previously, after surface treatment with 0.3% by dry weight of a polyquaternary amine. As seen in FIG. 2, the total water absorbency measured at the 30 minute interval increased from 3.19 gms of water absorbed per 0.1 gm of polymer to 3.78 gms of water absorbed per 0.1 gm of polymer an increase of over 18%. Likewise, the total amount of water retained increased from 2.63 gm to 2.89 gm per 0.1 gm of polymer, or an increase of about 10%. The absorption rates, tested at 1 minute and 3 minutes, also showed increases of over 26% and of over 10% for the surface treated polymer compared to the untreated polymer. These and the other results listed in TABLE I are most surprising in the art of water absorbent polymers.

This same procedure outlined above was used to determine initial water retention, total water-retention and total absorbency of the polymers of the present invention wherein the acrylate is polymerized in the presence of a styrene-maleic anhydride resin. The polymers made according to the method of the present invention were compared to acrylate polymers synthesized in the absence of styrene-maleic anhydride resins and also compared to acrylate-styrene copolymers for their water-absorption and water-retention capabilities. For the polymers that were treated with a polyquarternary amine, the polymer was treated with the listed percentage of MAGNIFLOCK 579C, a polyquaternary amine with highly cationic properties and of moderage, e.g., 2000-4000, molecular weight.

For example, the copolymer of FIG. 3 was prepared in the same manner as that of FIG. 1 except with the addition of styrene by copolymerizing the following mixed monomer composition:

| CHEMICAL | PARTS BY WT. | PERCENT |
|---|---|---|
| Acrylic Acid | 16.96 | 53.28 |
| Ammonium Hydroxide (30% aqueous ammonia) | 4.20 | 13.20 |
| Potassium hydroxide | 4.20 | 13.20 |
| Styrene | 0.65 | 2.04 |
| 4-t-butylazo-4'-cyanovaleric acid | 0.13 | 0.41 |
| GPTA (glyceryl propoxytriacrylate) MW = 428.5 | 0.002 | 0.01 |
| Ammonium carbonate | 3.31 | 10.40 |
| Water | 2.38 | 7.49 |
| TOTAL | 31.83 | 100.00 |

As shown in FIG. 3, when the mixed monomer solution contains 2% styrene based on the weight of acrylic acid, the total water-absorbency measured at the 30 minute time interval increased from a value of 3.19 (see FIG. 1 homopolymer data) to a value of 4.21 and the total amount of water retained increased from a value of 2.63 (see FIG. 1 homopolymer data) to a value of 3.11 representing an increase in total water-absorbed of more than 30% and an increase in total water retention of almost 20%. These results, and similar results shown in FIGS. 4 through 6, demonstrate the effect on water-absorbency and water-retention of copolymerizing styrene with neutralized acrylic acid. With reference to the following TABLE 1, FIGS. 7-14, wherein a styrene-maleic anhydride resin is present in the monomer solution, shows unexpectedly improved water-absorption and water-retention properties compared to the polymers of FIGS. 1-6 that do not include the styrene-maleic anhydride resin.

TABLE I

| Polymer (Amount of Surface Treatment) | Gm. H₂O Absorbed/.1 g Polymer | | | | |
|---|---|---|---|---|---|
| | .5 psi after 1 min. | .5 psi after 3 min. | .5 psi after 20 min. | .02 psi after 30 min. | .5 psi after 35 min. |
| 1. Neutralized polyacrylic acid (no treatment) | 1.45 | 1.72 | 2.22 | 3.19 | 2.63 |
| 2. Neutralized polyacrylic acid (0.3% polyquat.) | 1.83 (26%) | 2.05 (19%) | 2.49 (12%) | 3.78 (18%) | 2.89 (10%) |
| 3. Neutralized polyacrylic acid 2% styrene (no treatment) | 1.46 | 1.61 | 2.19 | 4.21 | 3.11 |
| 4. Neutralized polyacrylic acid 2% styrene (0.3% polyquat) | 2.34 (60%) | 2.72 (69%) | 2.93 (33%) | 5.20 (23%) | 3.70 (19%) |
| 5. Neutralized polyacrylic acid 4% styrene (no treatment) | 1.56 | 1.75 | 2.19 | 4.62 | 3.41 |
| 6. Neutralized polyacrylic acid 4% styrene (0.5% polyquat.) | 2.11 (35%) | 2.54 (45%) | 2.85 (30%) | 5.22 (13%) | 3.73 (9%) |
| 7. Neutralized polyacrylic acid 4.3% styrene-maleic anhydride resin (3:1 ratio) (no treatment) | 1.58 | 1.83 | 2.55 | 4.85 | 3.78 |
| 8. Neutralized polyacrylic acid 4.3% styrene-maleic anhydride resin (3:1 ratio) (0.6% polyquat.) | 1.59 (1%) | 1.85 (1%) | 2.53 (−1%) | 5.54 (14%) | 4.51 (19%) |
| 9. Neutralized polyacrylic acid 4.8% styrene-maleic anhydride resin (2:1 ratio) (no treatment) | 1.54 | 1.78 | 2.60 | 3.86 | 3.36 |
| 10. Neutralized polyacrylic acid 4.8% styrene-maleic anhydride resin (2:1 ratio) (0.6% polyquat.) | 1.83 (18%) | 2.03 (14%) | 2.61 (0.5%) | 5.36 (39%) | 4.15 (24%) |
| 11. Neutralized polyacrylic acid 4.3% sulfonated styrene-maleic anhydride resin (3:1 ratio) (no treatment) | 1.44 | 1.77 | 2.49 | 3.67 | 3.55 |
| 12. Neutralized polyacrylic acid 4.3% sulfonated styrene-maleic anhydride resin (3:1 ratio) (0.3% polyquat.) | 2.12 (47%) | 2.36 (33%) | 2.87 (15%) | 4.50 (23%) | 3.55 (—) |
| 13. Neutralized polyacrylic acid 4.8% esterified styrene-maleic anhydride resin (2:1 ratio) (no treatment) | 1.52 | 1.76 | 2.66 | 3.79 | 3.52 |
| 14. Neutralized polyacrylic acid 4.8% esterified styrene-maleic anhydride resin (2:1 ratio) (0.6% polyquat.) | 1.82 (20%) | 2.08 (18%) | 3.21 (21%) | 5.10 (35%) | 4.67 (33%) |

( ) = % improvement

As seen in FIG. 7, the neutralized polyacrylic acid including 4.3% styrene-maleic anhydride resin (3:1) ratio showed a 30% increase in total water absorption compared to FIG. 1 (4.85 gms absorbed compared to 3.19 gms) and showed a 44% increase in total water-retention compared to FIG. 1 (3.78 gms compared to 2.63 gms). Furthermore, From FIG. 8, surface-treating the polymer used in FIG. 7 with 0.6% of a polyquaternary amine showed a total absorbence of 5.54 g, or a 74% and a 14% improvement or FIGS. 1 and 7, respectively; and a total water-retention of 4.51 g, or a 71% and a 19% improvement over FIGS. 1 and 7.

Similarly, comparing FIG. 7 to FIGS. 3 and 5, an improvement is seen by including 4.3% of the 3:1 styrene-maleic anhydride resin (styrene content in the resin of 3.2% by weight) compared to copolymerizing 2% and 4% styrene by wt. into the resin (FIGS. 3 and 5, respectively). For example, FIG. 7 (3.2% styrene in the form of a styrene-maleic anhydride resin) showed a 15% increase in total water absorption compared to FIG. 3 (2% styrene copolymer) and a 5% increase compared to FIG. 5 (4% styrene copolymer). In addition, FIG. 7 exhibited an increase in total water-retention of 22% and 11% over FIGS. 3 and 5, respectively.

Figure 13:
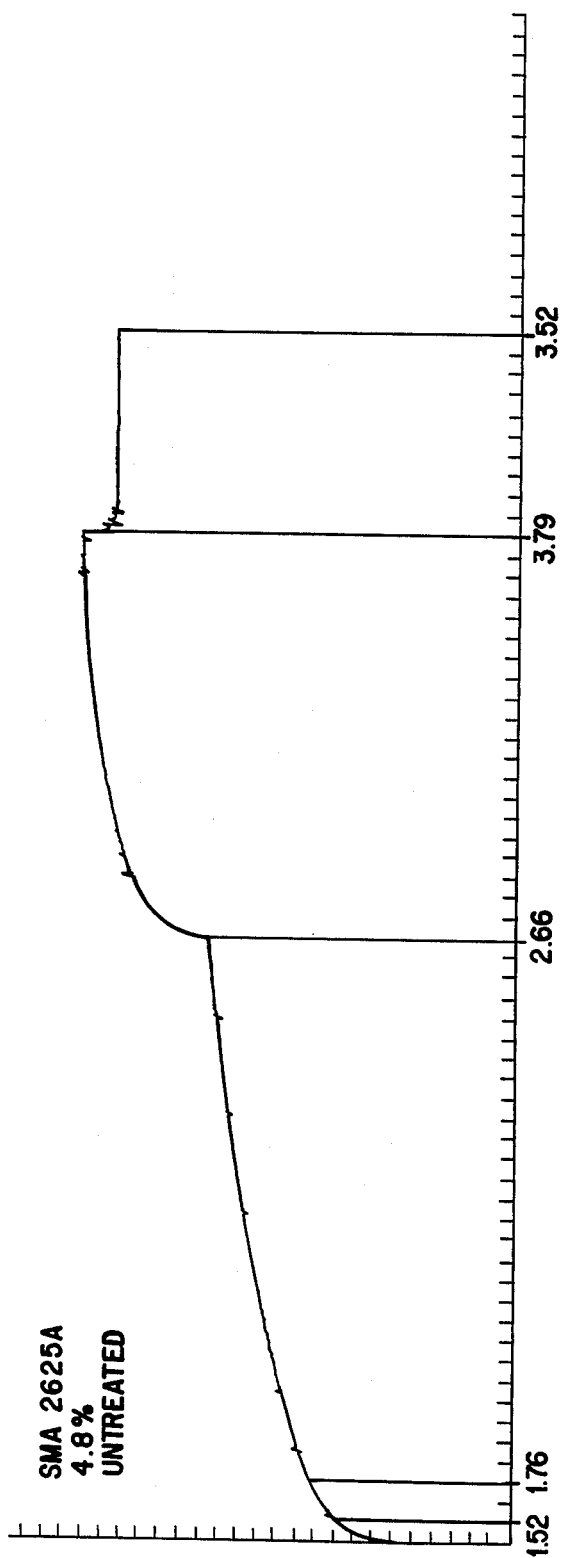
FIGS. 13 and 14 are GATS graphs showing water absorbency vs. time for an acrylate polymer including 4.8% of a partially esterfied styrene-maleic anhydride resin (2:1 ratio of styrene to maleic anhydride) without surface treatment and with surface treatment by 0.6% polyquaternary amine (by dry weight), respectively.
Figure 14:
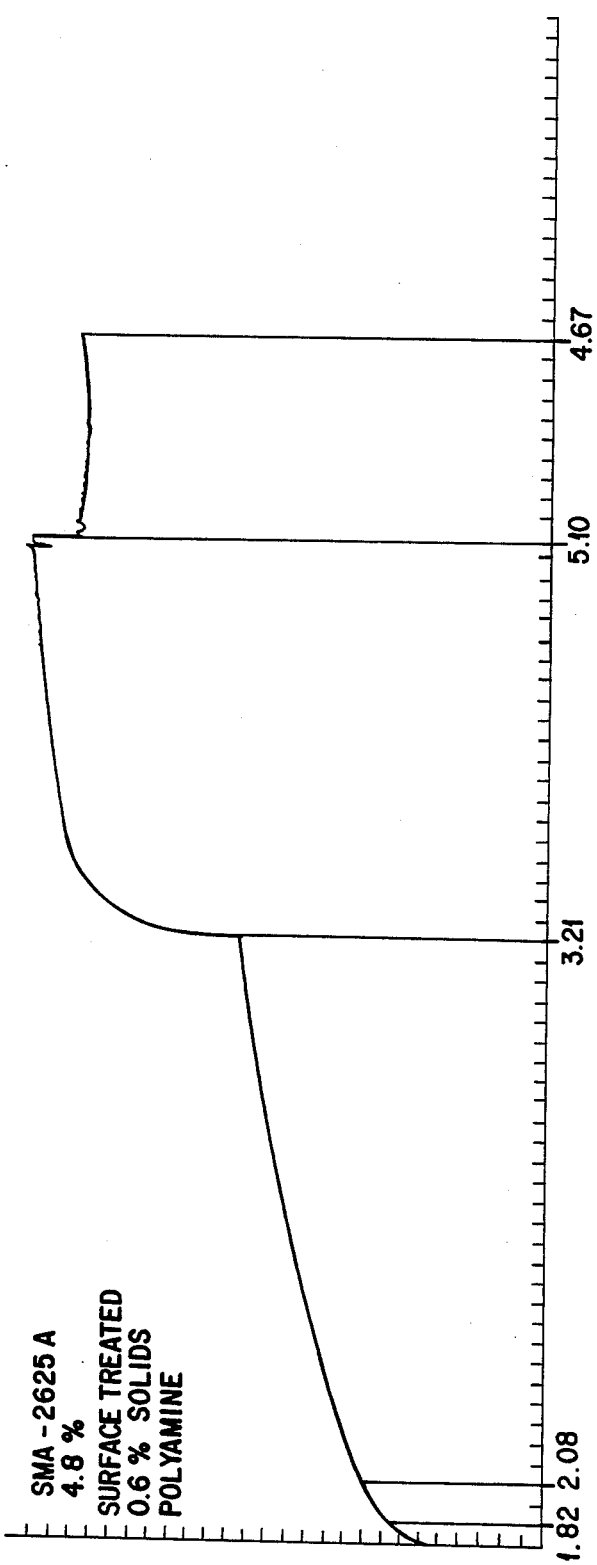

Improved water absorption and water-retention results are observed for polyacrylates including a styrene-maleic anhydride resin having a 2:1 styrenemaleic anhydride ratio (FIG. 9 and 10); for a sulfonated styrene-maleic anhydride resin with a 3:1 ration (FIGS. 11 and 12); and for an esterified styrenemaleic anhydride resin with a 2:1 ratio (FIGS. 13 and 14). For each polymer, surface treatment with a polyquaternary amine further improved with water absorption and water-retention of the polymers.

The present invention, utilizing styrenemaleic anhydride resins will be described in greater detail with reference to the following examples.

EXAMPLE 1

The following are combined, wherein percents are weight percents based on the total weight of the solution formed, 48.01% acrylic acid and 2.07% styrene-maleic anhydride resin (3:1 ratio) based on the weight of acrylic acid first, then 30.66% of aqueous potassium hydroxide (53.2% KOH) and 11.82% potassium carbonate serving as neutralizing agents. Thereafter 0.02% of N,N-methylenebisacrylamide as a polyvinyl monomer is added to prepare an aqueous solution of potassium acrylate and neutralized styrenemaleic anhydride resin having a neutralization degree of about 80% and a combined monomer-resin concentration of 53.10 wt. %.

The aqueous solution is maintained at 70° C., and with the solution is admixed 0.36% of 2,2'-azobis-(2-amidino-propane)hydrochloride and 0.20% of ammonium persulfate both in an aqueous solution. The final solution is as follows:

| CHEMICALS | |
|---|---|
| Acrylic Acid | 48.01% |
| Styrene-Maleic Anhydride Resin | 2.07% |
| (3:1 styrene to maleic anhydride ratio) | (1.55% as styrene, 0.52% as maleic anhydride) |
| Potassium Hydroxide | 16.31% |
| Potassium Carbonate | 11.82% |
| N,N—Methylenebisacrylamide | 0.02% |
| Azo Polymerization Initiators | 0.36% |
| Ammonium Persulfate | 0.20% |
| Water | 21.06% |
| TOTAL | 100.00 |

The mixture is poured onto a traveling endless belt and spread thereover in the form of a layer about 10 mm in thickness. The reaction then is initiated by adding 0.14% by weight of an aqueous solution containing 33% by wt. of a 50/50 mixture of sodium thiosulfate and ammonium persulfate redox initiators to the monomer/styrene-maleic anhydride solution. About 30 seconds thereafter, the mixture starts to polymerize, and the reaction is completed in about 1 minute. The maximum temperature of the mixture during the reaction is about 120° C.

The polymer is allowed to complete curing for about 30 minutes at ambient temperature to give a dry solid strip of potassium polyacrylate incorporating the neutralized styrene-maleic anhydride resin product, and having a water content of 11% and a residual monomer concentration of less than 1000 ppm. The solid strip of polymer is pulverized into a powder, then surface treated by evenly spraying a methanol solution containing from about 5% by weight of a polyquaternary amine over the powder until it is surface treated with from about 0.6% of the polyquaternary amine by dry weight. A separate blending operation, or the packaging operation, serves to evenly distribute the surface-treated resin throughout the product. This same surface-treating procedure is used for crosslinked polymers of acrylic acid or the crosslinked copolymers of acrylic acid with acrylamide or other ethylenically unsaturated monomers by evenly spraying a methanol solution containing from about 0.1% to about 20% by weight of a polyquaternary amine over the powder until it is surface treated with from about 0.1% to about 5% of the polyquaternary amine by dry weight.

EXAMPLES 2 TO 5

Polymers are prepared in the same manner as in Example 1 with the exception of varying at least one of the combined concentration of monomers, the amount of polyvinyl monomer (N,N-methylenebisacrylamide), the kind and amount of styrene-maleic anhydride resin, the kind and amount (degree of neutralization) of neutralizing agent, and the amounts based on the combined amount of the monomers, of azo polymerization initiator. One-half of the polymerized polymer solid was surface-treated as in Example 1, and one-half was left untreated. The following compositions are polymerizable:

EXAMPLE 2

| Acrylic Acid | 47.90% |
|---|---|
| Styrene-Maleic Anhydride Resin | 2.31% |
| (2:1 ratio) | (1.55% as styrene, 0.76% as maleic anhydride) |
| Potassium Hydroxide | 16.26% |
| Potassium Carbonate | 11.80% |
| N,N—methylenebisacrylamide | 0.02% |
| Azo Polymerization Initiator | 0.36% |
| Ammonium Persulfate | 0.20% |
| Water | 21.15% |
| TOTAL | 100.00% |

EXAMPLE 3

| Acrylic Acid | 49.46% |
|---|---|
| Styrene-Maleic Anhydride Resin | 2.93% |
| (3:1) | (2.20% as styrene, 0.73% as maleic anhydride) |
| Potassium Hydroxide | 11.25% |
| Potassium Carbonate | 15.01% |
| N,N—methylenebisacrylamide | 0.023% |
| Azo Polymerization Initiator | 0.36% |
| Ammonium Persulfate | 0.20% |
| Water | 20.77% |
| TOTAL | 100.00% |

EXAMPLE 4

| Acrylic Acid | 57.95% |
|---|---|
| Styrene-Maleic Anhydride Resin | 1.16% |
| (1:1 ratio) | (.58% as styrene; .58% as maleic anhydride) |
| Potassium Hydroxide | 14.51% |
| Ammonium Carbonate | 11.61% |
| GPTA | 0.02% |
| Azo polymerization initiator | 0.24% |
| Ammonium hydroxide | 14.51% |
| (30% wt. aqueous) | |
| TOTAL | 100.00% |

EXAMPLE 5

| Acrylic Acid | 57.27% |
|---|---|
| Styrene-Maleic Anhydride Resin | 2.30% |
| (1:1 ratio) | (1.15% as styrene; 1.15% as maleic anhydride) |
| Potassium Hydroxide | 14.35% |
| Ammonium Carbonate | 11.48% |
| N,N—methylenebisacrylamide | 0.11% |
| Azo Polymerization Initiator | 0.14% |
| Ammonium hydroxide | 14.35% |
| (30% wt. aqueous) | |
| TOTAL | 100.00% |

The amount of polyvinyl monomer listed is expressed in % by weight based on the combined amount of potassium acrylate, free acrylic acid, styrene and the polyvinyl monomer, and the concentration of initiator is expressed in % by weight based on the combined amount by weight (calculated as solids) of the monomers and the initiator, the same as hereinbefore.

EXAMPLE 6

To 22.2 g of deionized water are added 71.1 g of acrylic acid and 4 g of styrene-maleic anhydride resin (3:1 ratio) first, then 49.5 g of potassium hydroxide having a purity of 85% and serving as a neutralizing agent, and thereafter 0.01 g of N,N-methylenebisacrylamide as a polyvinyl monomer to prepare an aqueous solution of potassium acrylate having a neutralization degree of 75%, partially neutralized styrene-maleic anhydride and a combined concentration of acrylate and styrene-maleic anhydride of about 75 wt.%.

The aqueous solution is maintained at 70° C., and with the solution are admixed 2.9 g of 18% aqueous solution of ammonium persulfate (0.67 wt. % based on the combined weight of the potassium acrylate, free acrylic acid, styrene-maleic anhydride resin and N,N-methylenebisacrylamide). The mixture of poured onto a traveling endless belt and spread thereover in the form of a layer about 10 mm in thickness. About 30 seconds thereafter, the mixture starts to polymerize, and the reaction is completed in about 1 minute. The maximum temperature of the mixture during the reaction is about 120° C.

The reaction gives a dry solid strip of crosslinked potassium polyacrylate homopolymer incorporating the styrene-maleic anhydride resin. The strip is made into a powder by a pulverizer; then surface treated with a 7% methanol solution of a polyquaternary amine to yield a polymer having a 0.3% polyquaternary surface treatment.

EXAMPLES 7 TO 10

Polymers are prepared in the same manner as in Example 6 with the exception of changing at least one of the amount of N,N-methylenebisacrylamide and the kind and amount of the polymerization initiator as listed in Table 1 below.

TABLE 1

| Ex. No. | Initiator Kind | Conc. | Amt. of Polyvinyl Monomer |
|---|---|---|---|
| 7 | 2,2'-azobis-(2-amidinopropane)dihydrochloride | 0.5 | 0.01 |
| 8 | 2,2'-azobis-(2-amidinopropane)dihydrochloride | 0.5 | 0.02 |
| 9 | 2,2'-azobis-(2-amidinopropane)dihydrochloride | 1.0 | 0.01 |
| 10 | 2,2'-azobis-(2-amidinopropane)dihydrochloride | 1.0 | 0.02 |

EXAMPLES 11 TO 18

Polymers are prepared in the same manner as in Example 1 except that the compounds listed in Table 2 below are used as polyvinyl monomers in the listed amounts.

TABLE 2

| Ex. No. | Polyvinyl Monomer Kind | Amount |
|---|---|---|
| 11 | Ethylene glycol diallyl ester | 0.01 |
| 12 | Ethylene glycol diallyl ester | 0.02 |
| 13 | Diethylenetriamine-diacrylamide | 0.01 |
| 14 | Diethylenetriamine-diacrylamide | 0.02 |
| 15 | N,N—methylene-bismethacrylamide | 0.01 |
| 16 | N,N—methylene-bismethacrylamide | 0.05 |
| 17 | Polyethylene glycol diacrylate* | 0.01 |
| 18 | Polyethylene glycol diacrylate* | 0.05 |

*Polyethylene glycol diacrylate used in Examples 17 and 18 is represented by the following formula:

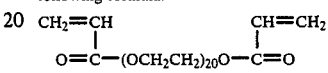

EXAMPLES 19 TO 22

Acrylic acid (71.1 g), 18.0 g of deionized water, 40.9 g of solid potassium hydroxide (water content 4%), 4.0 grams styrene-maleic anhydride resin (3:1 ratio), and 5.2 g acetone (5 wt. % based on the monomers) are mixed together, and the mixture is maintained at 75° C. With the mixture is further admixed 4.0 g of 10% aqueous solution of 2,2'-azobis(2-amidinopropane)dihydrochloride. The resulting mixture is immediately poured onto a traveling endless belt and spread thereover to a thickness of 5 mm. About 15 seconds later, the mixture starts to polymerize, and the polymerization is completed in about 30 seconds. The maximum temperature of the mixture during the reaction is 130° to 135° C.

The reaction gives a dry strip of crosslinked potassium polyacrylate product containing the styrenemaleic anhydride resin. The product is pulverized to a powder 20 to 100 mesh in particle size. The polymer was not surface treated.

The same procedure as above is repeated with use of the other solvents.

EXAMPLE 23

An aqueous monomer solution is prepared in the same manner as in examples 19 to 22 with the exception of not using any organic solvent and using 23.2 g of deionized water. The solution is thereafter subjected to polymerization in the same manner as in these examples to obtain a powder of dry solid, that was subsequently surface treated.

EXAMPLES 24 AND 26

Water absorbing resin solids are prepared in the same manner as in Example 19 with the exception of using 3, 5 or 10 wt. %, based on the monomers and styrene-maleic anhydride resin, of methanol in place of 5.2 g of acetone and varying the amount of deionized water so that the combined amount of the water and the methanol is 23.2 g.

EXAMPLE 27

89.4 gr. of acrylic acid and 9.9 gr. of acrylamide are dissolved in 118.8 gr. of distilled water and 52.6 gr. of KOH is added for 75 mole percent partial neuturalization of acrylic acid. 2.67 grams of styrene-maleic anhydride resin (3:1 ratio) is added to the solution. 0.018 gr. of N,N'-methylenebisacrylamide is added as the polyvinyl monomer, and 0.08 gr. of ammonium persulfate and 0.08 gr. of sodium thiosulfate are added as the polymerization initiators. The initial temperature of the mixed monomer solution is 30° C. After polymerization, the solid was surface treated to yield a 0.6% by wt. surface-treated product.

EXAMPLE 28

47.1 gr. of acrylic acid and 11.9 gr. of acrylamide are dissolved in 252.1 gr. of distilled water and 27.4 gr. of aqueous ammonia is added for 70 mole percent partial neutralization of acrylic acid. In this case, the concentration of the ammonia is 29 weight percent. In addition, two grams of styrenemaleic anhydride resin (1:1 ratio) and 0.006 gr. of N,N'-methylenebisacrylamide are added. The polymerization is performed with the addition of 0.048 gr. of ammonium persulfate and 0.048 gr. of sodium thiosulfate for initiation. In this case, the initial temperature of the mixed monomer solution is 30° C.

EXAMPLE 29

51.9 gr. of acrylic acid and 17.3 gr. of acrylamide are dissolved in 25 gr. of distilled water and they are partially neutralized 80 mole percent with the addition of 32.8 gr. of KOH. 3.3 grams of styrene-maleic anhydride resin (3:1 ratio) and 0.007 gr. of N,N'-methylenebisacrylamide is added. For the polymerization catalyst 0.7 gr. of 2,2'-azobisisobutyronitrile dissolved in 10 cc. of acetone is added. The solution is kept at 80° C. in a TEFLON coated, glass fiber reaction chamber until completion of polymerization and crosslinking reactions yielding a solid resin. The resin is then surface treated with a polyquaternary amine.

EXAMPLE 30

17.3 gr. of acrylamide is dissolved in 52.0 gr. of acrylic acid and partial (70 mole percent) neutralization of acrylic acid is accomplished by the addition of 30 gr. of aqueous ammonia having a concentration of 29 weight percent. In this case, for the polyvinyl monomer, 0.007 gr. of N,N'-methylenebisacrylamide is added. 1.4 grams of styrene-maleic anhydride resin (1:1 ratio) is added for copolymerization and, as the catalyst, 0.7 gr. of 2,2'-azobis(2amidinopropane)dihydrochloride dissolved in 8 gr. of distilled water is added. The polymerization is started at 80° C. to yield a solid resin.

EXAMPLE 31

20 kg. of acrylic acid and 6 kg. of acrylamide are dissolved in 9.5 kg. of distilled water and the acrylic acid is partially neutralized with 12 kg. of KOH. 0.036 kg. of methylenebisacrylamide as a polyvinyl monomer was added as well as 4 kg. of styrene-maleic anhydride resin (3:1 ratio) to provide an aqueous mixed monomer solution. The mixed monomer solution is mixed with 0.28 kg. of 2,2'-azobisisobutyronitrile, dissolved in 2 kg. of acetone as a polymerization initiator. This mixture at a temperature of 60° C. is transferred on an endless belt (600–700 mm. in width, and 7 m. in length) at a thickness of about 1 cm. The polymerization is initiated promptly on the belt resulting in a solid resin.

EXAMPLE 32

123.3 gr. of acrylamide is dissolved in 48.2 gr. of acrylic acid and 28.0 gr. of aqueous ammonia (29% concentration) is added for 70 mole percent neutralization of the acrylic acid. Next, 0.01 gr. of N,N'-methylenebisacrylamide and 7.0 grams of styrene-maleic anhydride resin (1:1 ratio) are added and stirred to homogenize. As an initiator, 0.7 gr. of 2,2'-azobis(2-amidinopropane)dihydrochloride dissolved in 5 gr. of distilled water is added. The polymerization is initiated in a TEFLON coated glass reaction chamber kept at 80° C., yielding a solid porous resin having a water content of less than 15% by weight. The pulverized solid is surface treated with 0.6% of a polyquaternary amine.

EXAMPLE 33

15.8 gr. of acrylamide is dissolved in 44.2 gr. of acrylic acid. 28.0 gr. of aqueous ammonia (29% concentration) is added to neutralize 70 mole percent of the acrylic acid. Then 20 grams of styrenemaleic anhydride resin (1:1 ratio) and 0.01 gr. of N,N'-methylenebisacrylamide are added. Next, as the initiator, 0.7 gr. of 2,2'-azobis(2-amidinopropane)dihydrochloride dissolved in 5 gr. of distilled water is added. The solution is kept at 80° C. and polymerization is initiated with increased temperature resulting in a solid, porous resin.

It will be understood that the present disclosure has been made only by way of preferred embodiment and that numerous changes in details of construction, combination, and arrangement of parts can be resorted to without departing from the spirit and scope of the invention as hereunder claimed.

What is claimed and sought to be secured by Letters Patent of the United States is:

1. A process for preparing a solid water absorbing resin of improved water absorbency comprising mixing a solution of (A) acrylic acid neutralized 70–100 mole percent; (B) a water-soluble styrene-maleic anhydride resin in an amount of about 1% to about 25% based on the weight of acrylic acid and neutralized 70–100 mole percent; and (C) a water-miscible to watersoluble polyvinyl monomer in a combined concentration of (A), (B) and (C) of at least 30 wt. %; with water to form a mixed solution and initiating polymerization of monomers (A) and (C) such that during polymerization, the exothermic heat of reaction is substantially the only heat energy used to accomplish polymerization, crosslinking and to drive off sufficient water to obtain a solid crosslinked resin including resin (B) and having a water content of 15 percent by weight or less.

2. A process as defined in claim 1 wherein the styrene-maleic anhydride resin (B) is essentially non-covalently bound to the solid crosslinked resin.

3. A process as defined in claim 1 wherein the styrene-maleic anhydride resin (B) is essentially homogeneously distributed throughout the solid crosslinked resin.

4. A process as defined in claim 1 wherein the combined concentration of the monomers (A) and (C) and resin (B) is at least 30 wt. % and less than 70 wt. %.

5. A process as defined in claim 1 wherein the styrene-maleic anhydride resin (B) is present in an amount of about 2% to about 12% based on the weight of acrylic acid.

6. A process as defined in claim 1 wherein the mixed solution has a temperature of 20° to 85° C. prior to polymerization.

7. A process as defined in claim 1 wherein monomer (C) is selected from the group consisting of N,N-methylenebisacrylamide and N,N-methylenebismethacrylamide.

8. A process as defined in claim 1 wherein the mixed solution contains 1 to 10 wt. % of an organic solvent based on the weight of monomers (A), (B) and (C).

9. A process as defined in claim 1 wherein the mixed solution further contains an organic solvent having a boiling point of 40° to 150° C.

10. A process as defined in claim 1 wherein the styrene-maleic anhydride resin has a styrene to maleic anhydride ratio ranging from approximately 3:1 to approximately 1:1.

11. A process as defined in claim 1 further comprising surface treating the solid crosslinked resin with a sufficient amount of a polyquaternary amine to substantially increase the water absorption of the solid crosslinked resin.

12. A process as defined in claim 11 wherein the resin is treated with from about 0.1% to about 5.0% by dry weight of a polyquaternary amine.

13. A process as defined in claim 11 wherein the resin is treated with from about 0.25% to about 2% by dry weight of a polyquaternary amine.

14. A process as defined in claim 11 wherein the polyquaternary amine has a molecular weight from about 200 to about 5000.

15. A process as defined in claim 11 wherein the polyquaternary amine has a molecular weight from about 300 to about 4000.

16. A process for preparing a solid, water absorbing, crosslinked resin of improved water absorbency comprising:
  combining a mixture of (A) potassium and/or ammonium acrylate; (B) neutralized, a water-soluble styrene-maleic anhydride resin in an amount of 1% to 25% based on the amount of acrylate computed based on the weight of acrylic acid; and (C) a polyvinyl monomer, with water in an amount of at least 30 combined weight percent of (A) plus (B) plus (C) based on the total weight of (A) plus (B) plus (C) plus water to form a mixture wherein the monomers of the the mixture consist essentially of (A) and (C);
  adding a polymerization initiator to said mixture capable of initiating, and in an amount sufficient to initiate polymerization of said mixture;
  copolymerizing said mixture while utilizing the exothermic heat of reaction as substantially the only non-ambient energy source to drive water away from said polyacrylate resin copolymer to form said crosslinked resin copolymer, including the styrene-maleic anhydride resin (B) and having a water content sufficiently low to be powdered without an intermediate drying step.

17. A process as defined in claim 16 wherein the styrene-maleic anhydride resin (B) is essentially noncovalently bound to the crosslinked resin copolymer.

18. A process as defined in claim 16 wherein the styrene-maleic anhydride resin (B) is essentially homogenously distributed throughout the crosslinked resin copolymer.

19. The process of claim 16 further including the step of adjusting the temperature of the mixture to a temperature of 25° to 85° C. prior to adding said polymerization initiator to said monomer mixture.

20. The process of claim 16 wherein said polymerization initiator is added in an amount of at lest 0.5% total by weight of (A) and (C).

21. The process of claim 16 wherein the water content of said crosslinked resin copolymer incorporating the styrene-maleic anhydride resin is not greater than about 10% by weight as recovered from the polymerized mixture, without an additional drying step.

22. The process of claim 16 further including combining a non-aqueous solvent having a boiling point of 40°–150° C. with said (A), (B) and (C) to form a porous resin.

23. The process of claim 16 including the step of pulverizing said crosslinked resin including the styrene-maleic anhydride resin to form a powder.

24. The process of claim 16 wherein the combined concentration of the monomers (A) and (B) and resin (B) is at least 30 wt. % and less than 70 wt. %.

25. The process of claim 16 wherein the styrene-maleic anhydride resin is neutralized and has a styrene to maleic anhydride ratio ranging from approximately 3:1 to 1:1.

26. The process of claim 16 further comprising contacting the crosslinked resin copolymer with a polyquaternary amine in an amount of from about 0.1% to about 5.0% based on the weight of the crosslinked resin copolymer.

27. The process of claim 16 including the step of pulverizing the crosslinked resin copolymer to form a powder prior to contacting said powder with a polyquaternary amine in an amount of about 0.1% to 5.0% based on the weight of said crosslinked resin copolymer.

28. The process of claim 16 wherein the crosslinked resin copolymer is treated with from about 0.25% to about 2.0% of a polyquaternary amine based on the weight of the crosslinked resin copolymer.

29. The process of claim 27 wherein the crosslinked resin copolymer is treated with from about 0.25% to about 2.0% of a polyquaternary amine based on the weight of said crosslinked resin copolymer.

30. The process of claim 16 wherein the polyquaternary amine has a molecular weight from about 200 to about 5000.

31. The process of claim 16 wherein the polyquaternary amine has a molecular weight from about 500 to about 3000.

32. The process of claim 16 wherein the polyquaternary amine is a condensation product of hexamethylenediamine, dimethylamine and epichlorohydrin; a condensation of dimethylamine and epichlorohydrin; or quaternized polyethylenimine.

33. The process of claim 16 wherein the polyquaternary amine is dispersed in methanol from about 0.1% to about 20% by weight before contacting the crosslinked resin copolymer.

34. A method of manufacturing a resin composition of improved water absorbency comprising mixing a solution of (A) acrylic acid, neutralized 70 to 100 mole percent, (B) a water-soluble styrene-maleic anhydride in an amount of 1% to 25% based on the weight of acrylic acid and neutralized 70 to 100 mole percent; and (C) acrylamide in a mole ratio of (A):(C) in the range of 70:30 to 100:0; (D) a water soluble or water miscible polyvinyl monomer crosslinking agent in an amount of 0.001 to 0.6 percent by weight of (A) plus (B) plus (C);

and water to form a mixed solution; and initiating polymerization of monomers (A), (C) and (D) such that during polymerization, the exothermic heat of reaction is substantially the only heat energy used to accomplish polymerization, crosslinking and to drive off sufficient water to form a water absorbing crosslinked polyacrylate resin composition including the styrene-maleic anhydride resin (B) and having a water content of 15 percent by weight or less.

35. The method of claim 34 wherein the styrene-maleic anhydride resin (B) is essentially non-covalently bound to the water absorbing crosslinked polyacrylate resin composition.

36. The method of claim 34 wherein the styrene-maleic anhydride resin is essentially homogenously distributed throughout the water absorbing crosslinked polyacrylate resin composition.

37. The method of claim 34 wherein the styrene-maleic anhydride resin (B) is present in an amount of about 2% to about 12% based on the weight of acrylic acid.

38. The method of claim 34 wherein the water content of said crosslinked polyacrylate resin composition including the styrene-maleic anhydride resin is not greater than about 10% by weight as recovered from the mixed solution after polymerization, without an additional drying step.

39. The method of claim 34 including depositing said solution including the monomer mixture, the styrene-maleic anhydride resin and said initiator onto a support surface in sheet form for polymerization and crosslinking, followed by pulverizing the resultant crosslinked resin to form a powder, and thereafter contacting said powder with a polyquaternary amine in an amount of from about 0.1% to 5.0% based on the weight of said powder.

40. A method of absorbing aqueous liquids comprising mixing a solution of (A) acrylic acid, neutralized 70 to 100 mole percent; (B) a water-soluble styrene-maleic anhydride resin in an amount of 1% to 25% based on the weight of acrylic acid and neutralized 70 to 100 mole percent; and (C) acrylamide in a mole ratio of acrylic acid:acrylamide in the range of 70:30 to 100:0; (D) a water soluble or water miscible polyvinyl monomer crosslinking agent in an amount of 0.001 to 0.6 percent by weight of (A) plus (B) plus (C); and water to form a mixed solution, wherein the concentration of (A), (B), (C) and (D) is below 70 percent by weight of the monomer solution prior to polymerization initiation; and initiating polymerization of monomers (A), (C) and (D) such that during polymerization, the exothermic heat of reaction is substantially the only heat energy used to accomplish polymerization, crosslinking and to drive off sufficient water to form a water absorbing crosslinked polyacrylate resin including the styrene-maleic anhydride resin (B) and having a water content of 15 percent by weight or less, and thereafter contacting said resin with an aqueous liquid to absorb improved quantities of said aqueous liquid into said resin.

41. The method of claim 40 further comprising contacting the crosslinked polyacrylate resin with a polyquaternary amine in an amount of from about 0.1% to about 5.0% based on the weight of said resin after forming the polyacrylate resin, and thereafter contacting said polyquaternary amine treated resin with an aqueous liquid to absorb said aqueous liquid into said resin.

* * * * *

UNITED STATES PATENT AND TRADEMARK OFFICE
CERTIFICATE OF CORRECTION

PATENT NO. : 4,820,773

DATED : April 11, 1989

INVENTOR(S) : William Alexander et al

It is certified that error appears in the above-identified patent and that said Letters Patent is hereby corrected as shown below:

Column 24, line 19, "(B)" should read --(C)--.

Signed and Sealed this

Third Day of October, 1989

Attest:

DONALD J. QUIGG

*Attesting Officer*   *Commissioner of Patents and Trademarks*